United States Patent [19]
Greenwald et al.

[11] Patent Number: 6,087,153
[45] Date of Patent: Jul. 11, 2000

[54] SEL-10 AND USES THEREOF

[75] Inventors: Iva Greenwald, New York; E. Jane Hubbard, Bronx, both of N.Y.

[73] Assignee: The Trustees of Columbia University in the City of New York, New York, N.Y.

[21] Appl. No.: 08/899,578

[22] Filed: Jul. 24, 1997

[51] Int. Cl.[7] .............................. C12N 1/20; C07H 17/00; C07K 14/00

[52] U.S. Cl. ................................ 435/252.33; 435/320.1; 536/23.1; 530/350

[58] Field of Search .......................... 530/350; 536/23.1; 435/69.1, 325, 252.33, 320.1

[56] References Cited

FOREIGN PATENT DOCUMENTS

WO 9711956   4/1997   WIPO .

OTHER PUBLICATIONS

Bai, C., et al. (1996) "SKP1 connets cell cycle regulators to the ubiquitin proteolysis machinery through a novel motif the F–box." *Cell* 86: 263–274.

Ellisen, L.W., et al. (1991) "TAN–1, the human homolog of the Drosophila Notch gene, is broken by chromosomal translocations in T lymphoblastic neoplasms." *Cell* 66: 649–661.

Gallahan, D. and R. Callahan (1987) "Mammary tumorigenesis in feral mice: identification of a new int locus in mouse mammary tumor virus (Czech II)—induced mammary tumors, *J. Virol.* 61: 66–74".

Grant, B. and I. Greenwald (1997) "Structure, function and expression of SEL–1, a negative regulator of LIN–12 and GLP–1 in *C. elegans*," *Development* 124: 637–644.

Greenwald, I., and G. Seydoux (1990) "Analysis of gain–of–function mutations of the Lin–12 gene of *Caenorhabditis elegans*." *Nature* 346: 197–199.

Greenwald, I., et al. (1983) "The lin–12 locus specifies cell fates in *Caenorhabditis elegans*." *Cell* 3: 435–444.

Kimble, J. (1981) "Alteration in cell lineage following laser ablation of cells in the somatic gonad of *Caenorhabdits elegans*." *Dev. Biol.* 87: 286–300.

King, R.W., et al. (1996) "How proteolysis drives the cell cycle." *Science* 274: 1652–1658.

Neer, E.J., et al. (1994) "The ancient regulatory–protein family of WD–repeat proteins." *Nature* 371: 297–300.

Robbins, J., et al. (1992) "Mouse mammary tumor gene int–3: a member of the Notch gene family transforms mammary epithelial cells." *J. Virol.* 66: 2594–2599.

Seydoux, G., and I. Greenwald (1989) "Cell autonomy of lin–12 frunction in a cell fate decision in *C. elegans*." *Cell* 57: 1237–1245.

Slen, J., et al. (1997) "Skeletal and CNS defects in presenilin–1–deficient mice." *Cell* 89: 629–639.

Sundaram, M., and I. Greenwald (1993b) "Suppressors of a lin–12 hypomorph define genes that interact with both lin–12 and glp–1 in *Caenorhabditis elegans*." *Genetics* 135: 765–783.

Tuck, S., and I. Greenwald (1995) "Lin–25, a gene required for vulval induction in *Caenorhabditis elegans*." *Genes Dev.* 9: 341–357.

Wong, P.C., et al. (1997) "Presenilin–1 is required for Notch and DII 1 expression in the paraxial mesoderm." *Nature* 387: 288–291.

PCT Notification of Transmittal of the International Search Report or the Declaration, dated Jan. 21, 1997 (Exhibit B);
PCT Written Opinion, dated Jul. 15, 1997 (Exhibit C).
R. Sherrington, et Al., Cloning of a Gene Bearing Missense Mutations in Early–Onset Familial Alzheimer's Disease, Jun. 29, 1995 *Nature* vol. 375:754–760 (Exhibit D).
Data Base Search, total of 3 pages (Exhibit E).
Wilson et al 1994 Nature 368:32–38.
Yochem et al 1987 J Mol Biol 195: 233–245.
Hubbard et al. Genes & Development 11: 3182–3193, Nov. 1997.

*Primary Examiner*—Karen Cochrane Carlson
*Attorney, Agent, or Firm*—John P. White; Cooper & Dunham LLP

[57] ABSTRACT

This invention provides an isolated nucleic acid molecule which encodes a wildtype or mutated SEL-10. This invention also provides a purified wild-type SEL-10 protein or a purified mutated SEL-10 protein. This invention also provides a method for production of an antibody capable of binding to wild-type SEL-10 or mutated SEL-10 protein. This invention also provides an antibody capable of specifically binding to wild-type SEL-10 or mutated SEL-10. This invention also provides a transgenic animal comprising the isolated nucleic molecule encoding SEL-10. This invention also provides a method for identifying a compound which is capable of ameliorating Alzheimer's disease. This invention also provides a method for determining whether a compound is capable of ameliorating Alzheimer's disease. This invention further provides a method for identifying a compound which is capable of treating cancer. This invention also provides a method for determining whether a compound is capable of treating cancer. This invention also provides a method for identifying a suppressor or enhancer that affects lin-12 or sel-12 activity in the same manner as sel-10. This invention also provides a method for producing suppressors of a sel-10 allele. This invention also provides a method for reversing the malignant phenotype of cells. This invention also provides a pharmaceutical composition effective in ameliorating Alzheimer's disease and treating cancer and methods of using such a pharmaceutical composition.

31 Claims, 9 Drawing Sheets

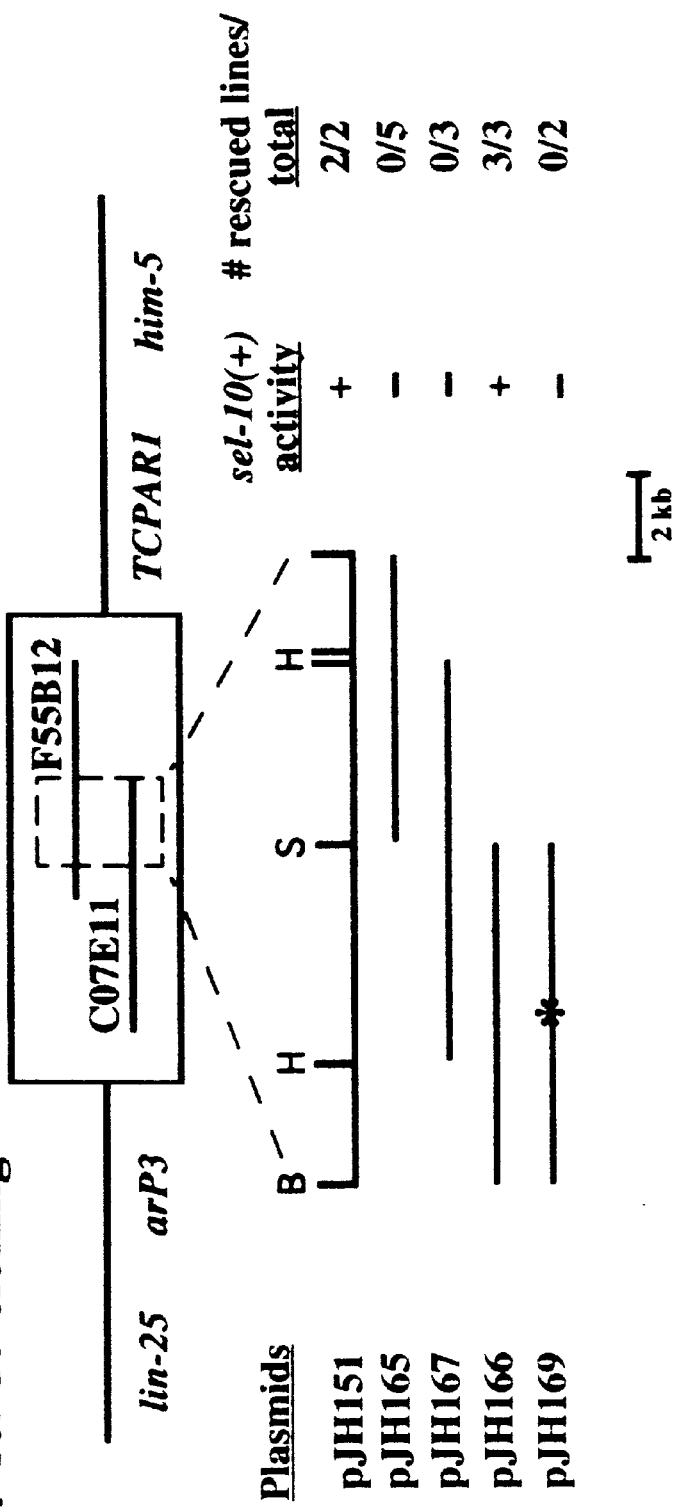
FIG. 1A *sel-10* cloning
FIG. 1B Predicted *sel-10* transcription unit

FIG. 2A

```
tcatagtttatcgactttccttttgtgttcaaattcttcattccaattcttttcagccat
                                                                          30
                                                                          90
 M  W  P  R  N  D  V  H  M  D  D  G  S  M  T  P  E  D  Q  E  P  V  T  D  N  D  M  E  Y  N
ATGTGGCCACGAAATGATGTACACATGGATGATGATGGATCAATGACACCGGAGGACCAGGAGCCTGTTACCGATAATGATATGGAATATAAT
                                                                          60
                                                                         180
 D  N  G  E  E  S  S  Y  S  N  G  S  S  S  S  Y  N  A  D  K  L  S  S  S  R  P  L  Q  H  K
GACAATGGAGAGGAAAGCTCGTACAGCAATGGCTCTTCTTCCAGCTACAATGCTGACAAATTATCGTCTTCCAGACCTTTGCAACACAAA
                                                                          90
                                                                         270
 L  D  L  S  A  S  P  S  R  N  N  D  L  N  P  R  V  E  H  L  I  A  L  F  K  D  L  S  S  A
CTTGATTTATCGGCTTCCTCCCCTCGAAACAACGACCTCAATCCGCGTGTGGAACATTTGATCGCATTATTCAAGGATCTATCAAGCGCG
                                                                         120
                                                                         360
 E  Q  M  D  A  F  T  R  L  L  Q  E  S  N  M  T  N  I  R  Q  L  R  A  I  I  E  P  H  F  Q
GAACAAATGGATGCATTCACACGTCTGCTTCAGGAATCCAACATGACAAATATTCGACAGCTGCGTGCCATTATTGAACCCCATTTCCAG
                                                                         150
                                                                         450
 R  D  F  L  S  C  L  P  V  E  L  G  M  K  I  L  H  N  L  T  G  Y  D  L  L  K  V  A  Q  V
CGTGATTTCCTCTCCTGCCTCCCTGTCGAGCTCGGAATGAAAATCCTTCACAATTTAACCGGATATGACCTGCTCAAAGTGGCACAGGTG
                                                                         180
                                                                         540
 S  K  N  W  K  L  I  S  E  I  D  K  I  W  K  S  L  G  V  E  E  F  K  H  H  P  D  P  T  D
TCGAAAAATTGGAAATTGATATCTGAAATTGACAAATTGGACAGAGTCTTGGTGTGAAGAGTTTAAACATCATCCAGATCCCACAGAC
                                                                         210
                                                                         630
 L  N  V  H  R  R  V  T  G  A  W  Q  G  T  A  I  A  A  G  V  T  I  P  D  H  I  Q  P  C  D
CGAGTTACTGGTGCTGGCAAGAACTGCAATTGCTGCTGGAGTCACTATTCCTGATCACATTCAGCCATGTCTTAATGTTCATCGA
                                                                         240
                                                                         720
 F  L  K  Q  K  F  G  D  I  F  E  R  A  A  D  K  S  R  Y  L  R  A  D  K  I  E  K  N  W
TTTCTAAAGTTGCAGAAGTTTGGAGATATCTTCGAGCCGCTGCTGACAAGTCACGTTATCTTGAAAATTGAAAAGAACTGG
```

FIG. 2B

```
                              ↑                    I
      N A N P I M G S A V L R G H E D H V I T C M Q I H D D V L V      270
      AATGCGAATCCAATTATGGGTCAGCAGTGCTACGAGGACACGAAGATCATGATGATGTCTTGGTG  810
                                          II
      T G S D D N T L K V W C I D K G E V M Y T L V G H T G G V W      300
      ACTGGATCTGACGATAACACTCTTAAAGTATGGTGTATTGACAAAGGAGAGTTATGTACACACTAGTCGGCCACACTGGAGGAGTTTGG  900
                                       *       S T V D G S L
      T S Q I S Q C G R Y I V S G S T D R T V K V W                    330
      ACATCACAGATTTCTCAATGCGGAAGATATATTGTTAGCGGGTCCACTGATAGAACTGTAAAAGTTTGGAGTACTGTAGATGGTTCACTT  990
              III
      L H T L Q G H T S T V R C M A M A G S I L V T G S R D T T L      360
      CTTCATACACTTCAAGGACACACATATACTTCGTGTTCCATACTTGTCACTGGATCACGAGATACCACTCTT  1080
                                       IV           ↑
      R V W D V E S G R H L A T L H G H H A A V R C Y Q F D G T        390
      CGTGTATGGGACGTAGAATCCGGACGTCACCTGGCAACTTTACATGGCCATCATGCAGCCGTTCGATGCGTTCAATTCGATGAACAACT  1170
                                                V
      V V S G G Y D F T V K I W N A H T G R C I R T L T G H N N R      420
      GTTGTTTCGGGAGGATATGATTTTACCGTTAAAATTTGGAATGCTCATACTGGGAGATGTCATAACGGTTCATAACAATAGA  1260
      V V Y S L L F E S E R S I V C S G S L D T S I R V W D F T R P    450
      GTTTATTCTCTCTTTTCTTGAAAGCGAGGATCGATCGTGTGCTCTCGGACACTTCAATTCGGTGTGGGATTTTACACGACCG  1350
```

FIG. 2C

```
                   VI
     E G Q E C V A L L Q G H T S L T S G M Q L R G N I L V S C N      480
GAAGGCCAAGAATGTGTGGCTCTTTTGCAAGGACACACCTCACTTACATCCGGAATGCAACTTCGAGGCAATATTCTCGTGTCATGCAAT    1440
                                                 VII
     E G T C V H M L S G H R S A I T S L Q      510
     D I H E G T C V H M L S G H R S A I T S L Q                                           1530
CACTTCAAGAGGAACTGTGTACACATGCTTTCTGGACATGCTTGTACACATGCTTTCTGGACACGAGGAACTGTGTACACATGCTTTCACTTCAA

A D S H V R V W D I E R G A L I R D L       540
GCAGATAGCCATGTTAGAGTATGGGATATTCACGAGGAGCTTGTGTACACATGCTTTCTGGACATGCTTGTACACATGCTTTC          1620
     ↑
 * W F G R N M V A T S S D D G T V K L W D
TGGTTTGGACGAAATATGGTAGCAACGAGTAGTGCCGATGAACTGTCAAATTGTGGGATATTGAGAGAGGTGCACTGATTCGAGATCTA
                                                                            ↑
     V T L D S G G N G G C I W R L C S T S T M L A C A V G S R N       570
GTAACTTTGGATTCGGAGGCAATGGTGCCCTGTATTGGCTGTGCTAGCTGTCTACGATGCTAGCGTGCCAGTCGGATCGTCGTAAC        1710

N T E E T K V I L L D F D A V Y P *                                                   587
                                                                                           1800
AACACCGAGGAGACCAAAGTTATCCTTCTCGACTTTGATGCTGTATACCCTTAAcgaattctcgaatctctgccctgtacatagaatgt
tcttgcttaggaactaatatttgtacacgatgccctcattttaaatcaacaatgctatcatatcatgaataagtctatcaaaaagcaacagt
attgaaacgtcaaatttgaggaaaaacgaattatgtgtctattcaactcgttatatccccgccactataattttttcttttttta
ctattttttgtcagattcgtctccacactctctcgattgttttcccattaagttatcggttttgattgattttatatttt
ttattcaaatgatgggctcactactcccagatttttgatttcttatacaatagttcagtcagtattgtagtcttatgtgactctttt
tgatctaatgagcttttttagtccctgcgttccctcttttgtcctttcattttcgcttaaaaactactgtcaaattcaaagttctac
cctcgacattgccttttttaaattttgtcttgttttatcgactatgccagacgtcattgtcgattaagtaggttaataacaattattt
cataataataatatcgattcgtgtcatccgtctatatgtgattctttt
```

Alignment of F-Box

FIG. 3A

```
SEL-10  127  LPVELGMKILHNLTGYDLLKVAQVSKNW.KLISEIDKIWKSLG
CDC4    278  LPFEISLKIFNYLQFEDIINSLGVSQNWNKIIRKSISLWKKLL
MD6      60  LPLELSFYLLKWLDPQTLLTCCLVSKQRNKVISACIEVWQTAC
```

FIG. 3B

Alignment of WD40 repeats

```
I    SEL-10  253  GHEDHVITCMQIHDDVLVISDDNTLKVWC
     CDC4    419  GHMTSVITCLQFEDNYVITADDKMIRVYD

II   SEL-10  294  GHTGGWTSQISQCGRYIVSGSTDRTVKVWS
     CDC4    460  GHDGGWALKYAHGG.ILVSSIDRTVRVND

III  SEL-10  336  GHTSIVRCMAMAG....SILVLSDTIRVWD
     CDC4    502  GHNSTVRCLDIVEYKNIKYIVSRDNLHVWK

IV   SEL-10  376  GHAAVRCVQFDGTTVVSGGYDFIVKIEN
     CDC4    569  GHMASVRTVSGHGNIVVSGSYDNTLIVWD

V    SEL-10  416  GHNNRVSLLFESERSIVCSGSLDTSRVWD
     CDC4    609  GHTDRIYSTIYDHERKRCISASMDTLRIWD

VI   SEL-10  461  GHTSLTSGMQLRGNILVSCNADSHVRVWD
     CDC4    671  GHTALVGLLRLSDKFLVSAAADGSIRGWD

VII  SEL-10  501  GHR..SAITSLQWFGRNMVATSSDDGTVKLWD
     CDC4    710  HHTNLSAITT.FYVSDNILVSGSENQFN.IYN
```

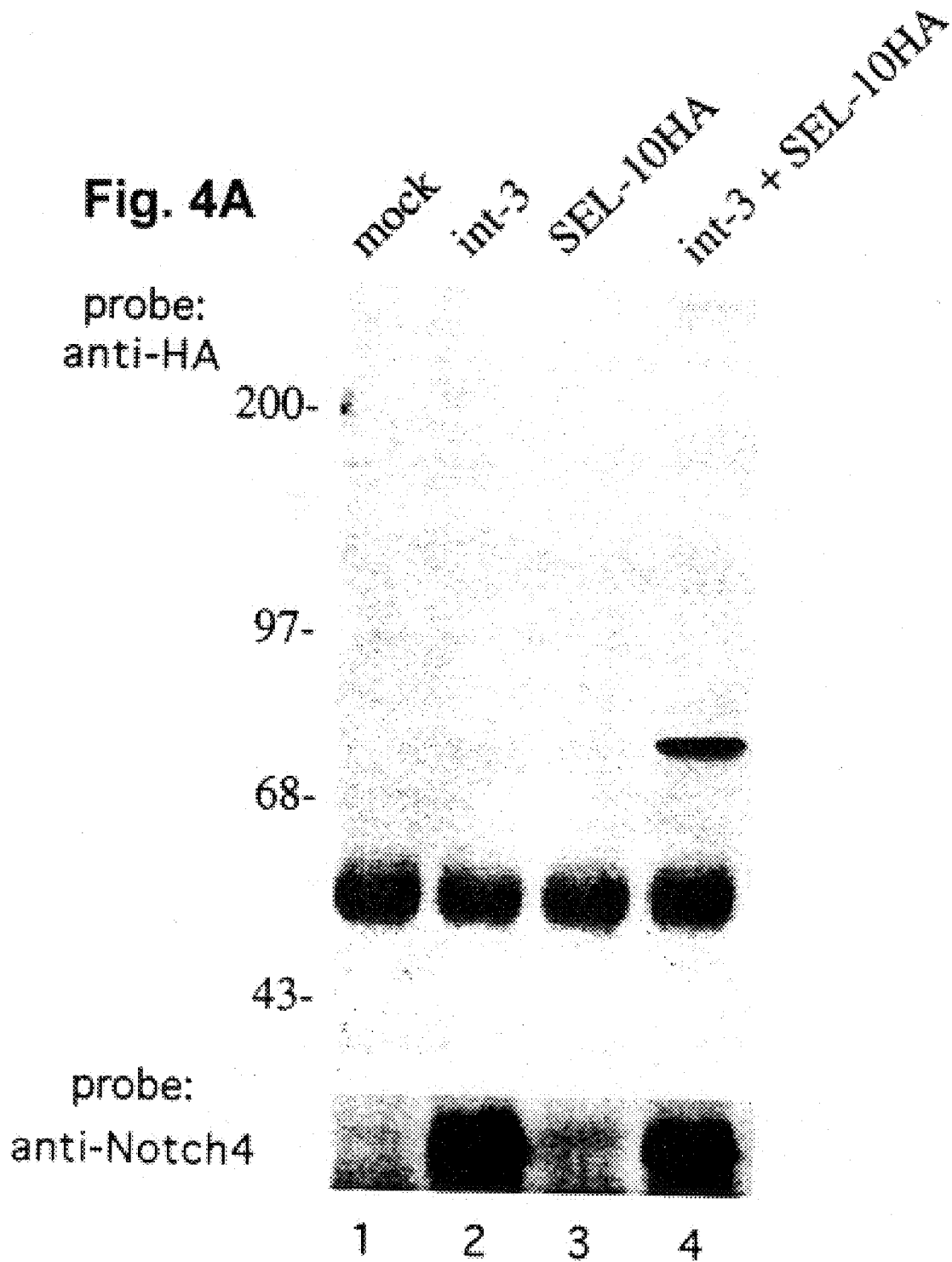

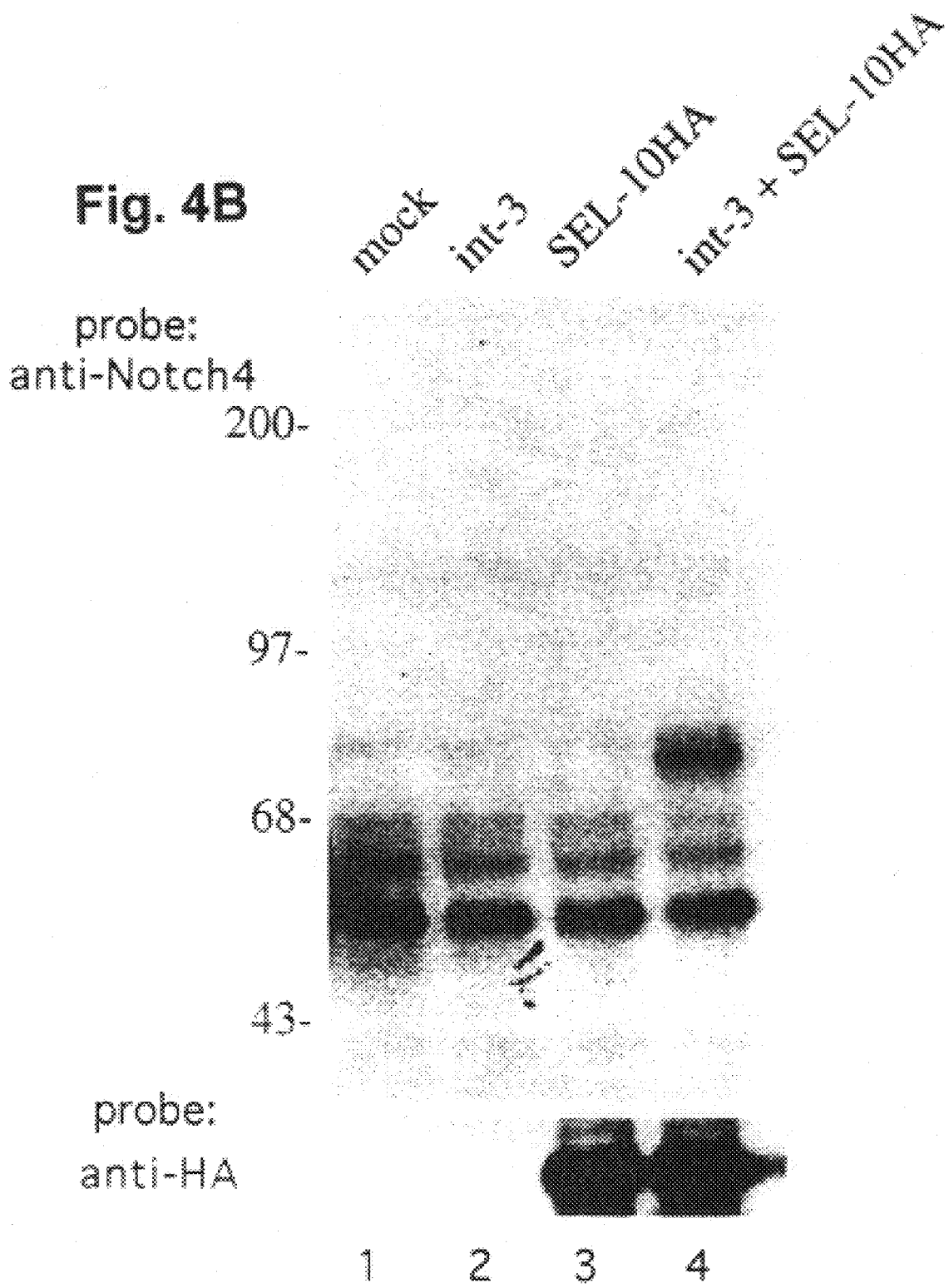

SEL-10 AND USES THEREOF

Part of the invention disclosed in this application was supported by the United States government, National Institute of Health grant GM 37602 and the U.S. Army Medical Research and National Command under grant DAMD 17-94-J-9410. Accordingly, the United States government has certain rights in this invention.

BACKGROUND OF THE INVENTION

Simple model organisms such as the free-living soil nematode C. elegans are experimentally tractable systems that can be used to provide insights into human development and disease. For example, genes associated with the development of cancer in humans have also been found in C. elegans. One of these human proto-oncogenes, termed TANT-1 (Ellisen et al., 1991), encodes a protein of the LIN-12/Notch family. This family was first identified by contemporaneous studies of the lin-12 gene in C. elegans and the Notch gene in Drosophila. It has been established that activating TAN-1 or a similar murine protein, Notch4, contributes to cancer formation. In C. elegans, activating LIN-12 affects cell fate decisions (Greenwald, e al., 1993; Greenwald and Seydoux, 1990; Struhl et al., 1993). Features common to all LIN-12/Notch proteins and their functions can be studied in C. elegans, and the results can be directly applied to mammals, with particular relevance to the study of cancer.

C. elegans can similarly serve as a model for processes involved in the development of Alzheimer's disease in humans. Two genes identified in linkage studies in humans encode related multipass transmembrane proteins, presenilins 1 and 2 (PS1 and PS2). The normal role of presenilins, and the mechanism by which mutant presenilins cause Alzheimer's disease, are not known. Genetic studies of the C. elegans presenilin SEL-12 (Levitan and Greenwald, 1995; Levitan et al., 1996) offer a powerful approach to understanding the normal role of presenilins. The basic biology of presenilins and Notch proteins is linked in both C. elegans and people: based on genetic interactions with lin-12, sel-12 has been shown to facilitate lin-12 signaling in C. elegans, and null mutations in the mouse PS1 and Notch1 genes have similar phenotypes (Wong et al., 1997; Shen et al., 1997).

The following is a detailed introduction to the first set of experiments, in which the sel-10 gene was identified as a regulator of lin-12 activity. In the first set of experiments, genetic interactions between sel-10 and lin-12 were discovered, and molecular and biochemical experiments were performed to elucidate the nature of the interaction. In a second set of experiments, interactions between sel-10 and sel-12 were discovered, consistent with the hypothesis that sel-10 possibly regulates sel-12 activity.

Many cell-cell interactions that specify cell fate are mediated by receptors of the LIN-12/Notch family and ligands of the Delta/Serrate/LAG-2 (DSL) family (reviewed Artavanis-Tsakonas et al., 1995). C. elegans affords an opportunity to study a simple case of lateral specification involving an interaction between two cells of the hermaphrodite gonad. These cells, named Z1.ppp and Z4.aaa, are initially equivalent in their developmental potential: each has an equal chance of becoming the anchor cell (AC), a terminally differentiated cell type that is necessary for vulval development, or a ventral uterine precursor cell (VU), which contributes descendants to the ventral uterus. However, in any given hermaphrodite, only one of these cells will become the AC, while the other becomes a VU (Kimble and Hirsh, 1979).

Laser ablation studies have shown that this process of lateral specification, the AC/VU decision, depends on interactions between Z1.ppp and Z4.aaa (Kimble, 1981; Seydoux and Greenwald, 1989). Furthermore, genetic studies have indicated that lin-12-mediated signalling controls the AC/VU decision: if lin-12 activity is inappropriately elevated, Z1.ppp and Z4.aaa become VUs, while if lin-12 activity is reduced, Z1.ppp and Z4.aaa become ACs (Greenwald et al., 1983). Genetic mosaic analysis (Seydoux and Greenwald, 1989) and reporter gene studies (Wilkinson et al., 1994) have indicated that both Z1.ppp and Z4.aaa initially express lin-12 and lag-2, but that a stochastic small variation in ligand and/or receptor activity is subsequently amplified by a feedback mechanism that influences lin-12 and lag-2 transcription. Thus, Z1.ppp and Z4.aaa assess their relative levels of lin-12 activity as part of the decision-making process, before either cell commits to the AC or VU fates, and the feedback mechanism ensures that only one of the two cells will become an AC and the other will become a VU.

It is striking that the receptors (lin-12/Notch proteins), ligands (DSL proteins), and at least one downstream signalling component (CBF1/Su(H)/LAG-1; see Christensen et al., 1996 and references therein) that mediate lateral specification are highly conserved in animals as distantly related as C. elegans, Drosophila, and vertebrates. Furthermore, a feedback mechanism like that first described for the AC/VU decision (Seydoux and Greenwald, 1989) also exists for a Notch-mediated lateral interaction in Drosophila (Heitzler and Simpson, 1991) and seems likely to operate in Notch-mediated lateral interactions in vertebrates (Austin et al., 1995; Chitnis et al., 1995; Washburn et al., 1997). The identification of genes that influence lin-12 activity during the AC/VU decision may reveal other conserved factors that participate in signal transduction or regulate the activity of lin-12/Notch proteins.

Genetic screens based on suppression or enhancement of lin-12 mutations have identified a number of genes that influence lin-12 activity. Here, sel-10 is described. It was first identified in a screen for suppressors of phenotypes associated with partial loss of lin-12 activity (Sundaram and Greenwald, 1993). sel-10 acts as a negative regulator of lin-12 signalling, and SEL-10 is a member of the CDC4 family of F box/WD40 repeat containing proteins. CDC4, the most extensively studied member of this family, is a Saccharomyces cerevisiae protein that is involved in the ubiquitin-mediated degradation of cell cycle regulators (reviewed in King et al., 1996).

The similarity of SEL-10 to CDC4 prompted investigation of the possibility that SEL-10 is involved in the ubiquitin-dependent turnover of LIN-12/Notch proteins. The experiments involved examining the biochemical effects of coexpressing C. elegans SEL-10 with a vertebrate LIN-12/Notch protein, Notch4. This vertebrate Notch gene was originally termed int-3, because it was identified by mouse mammary tumor virus insertions into a cellular gene (Gallahan and Callahan, 1989). In int-3 mutants, the viral long terminal repeat promotes expression of a truncated transcript that encodes a protein similar to the intracellular domains of LIN-12/Notch proteins (Robbins et al., 1992). The complete sequence of the gene defined by int3 revealed that the extracellular domain of the predicted protein also has the hallmarks of LIN-12/Notch proteins, and hence the gene is now known as Notch4 (Uyttendaele et al., 1996). During normal development, Notch4 expression is restricted primarily to endothelial cells (Uyttendaele et al., 1996). In int-3 mutants, the inappropriate expression of a truncated transcript encoding the intracellular domain of Notch4 in mammary epithelia may alter stem cell fate decisions, thereby contributing to the development of cancer. Furthermore, at least one human cancer, T cell acute lymphoblastic leukemia, has been associated with expression of a comparable truncated Notch protein (Ellisen et al., 1991), suggesting that inappropriate Notch activity could contribute to the development of a variety of tumors.

C. elegans SEL-10 physically interacts with murine Notch4 and causes a reduction in the steady-state levels of the murine Notch4 intracellular domain. Results suggest that the negative regulation of LIN-12/Notch by SEL-10 is an evolutionarily conserved feature, given the striking parallels between the effect of sel-10 activity on lin-12 in C. elegans and the effect of SEL-10 expression on Notch4 stability in mammalian tissue culture. Furthermore, the role of vertebrate Notch genes in oncogenesis suggests that vertebrate sel-10 counterparts may behave as tumor suppressors.

SUMMARY OF THE INVENTION

This invention provides an isolated nucleic acid molecule encoding a SEL-10.

This invention also provides a purified wild-type SEL-10 protein or purified wild-type SEL-10 fragment thereof or a purified mutated SEL-10 protein or purified mutated SEL-10 fragment thereof.

This invention also provides for a method for production of an antibody capable of binding to wild-type SEL-10 or mutated SEL-10 protein comprising a) administering an amount of the purified protein or fragment of wild-type SEL-10 or mutated SEL-10 to a suitable animal effective to produce an antibody against wild-type SEL-10 or mutated SEL-10 protein in the animal; and b) testing the produced antibody for capability to bind wild-type SEL-10 or mutated SEL-10.

This invention also provides for a method for production of an antibody capable of binding to wild-type SEL-10 or mutated SEL-10 protein.

This invention further provides for an antibody capable of specifically binding to wild-type SEL-10 or mutated SEL-10.

This invention also provides a transgenic animal comprising the isolated nucleic molecule encoding SEL-10.

This invention also provides a method for identifying a compound which is capable of ameliorating Alzheimer's disease.

This invention also provides various methods for determining whether a compound is capable of ameliorating Alzheimer's disease.

This invention further provides a method for identifying a compound which is capable of treating cancer.

This invention also provides for various methods for determining whether a compound is capable of treating cancer.

This invention further provides a method for identifying a suppressor or an enhancer that affects lin-12 or sel-12 activity in the same manner as sel-10, and the suppressor or enhancer so identified.

This invention also provides a method for producing enhancers of a sel-10 allele and the enhancer so produced.

This invention also provides a method for reversing the malignant phenotype of cells.

This invention also provides a pharmaceutical composition identified as being capable of amelioraing Alzheimer's disease. This invention also provides a pharmaceutical composition identified as being capable of treating cancer and various methods of ameliorating Alzheimer's diesease or treating cancer which comprises administering the above-described pharmaceutical compositions.

BRIEF DESCRIPTION OF FIGURES

FIGS. 1A and 1B. Molecular cloning of sel-10.

Figure 5:
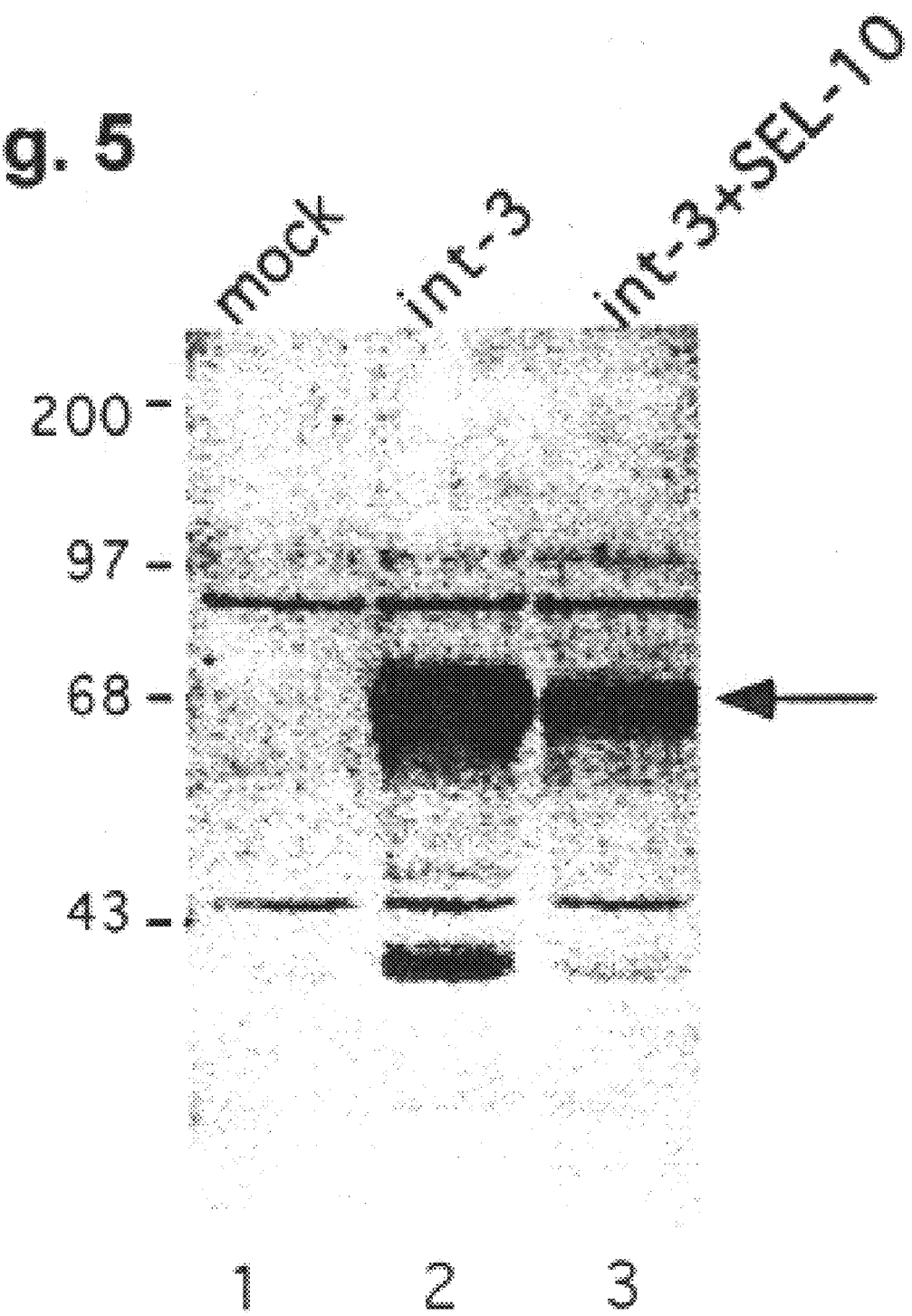

See Experimental Procedures for details of rescue assays, plasmid constructions, and molecular analysis. Genetic markers used to map sel-10 are italicized, and two cosmids that contain sel-10 sequences are shown in the box. The cosmid C07E11 and derivatives were tested for rescue. pJH169 is identical to pJH166 except that it contains a stop codon (indicated by an asterisk) in the predicted coding sequence after codon 172. Restriction sites are B, BamHI; H, HindIII; S, SalI.

1A. Restriction map of sel-10.

1B. Predicted sel-10 transcription unit.

FIGS. 2A–2C. cDNA sequence and predicted protein product of sel-10 (SEQ ID NO: 1), and (SEQ ID NO: 2).

Splice junctions are indicated by arrows below the DNA sequence. The first arrow indicates the SL1 splice junction. The F-Box (Kumar and Paietta, 1995, Bai et al., 1996) is overlined and underlined and the WD40 repeats are underlined and labelled in the Figure. The lesions in sel-10(ar41) and sel-10(ar28) are indicated with bold letters in the nucleotide sequence and a bold asterisk above the amino acid; both are G to A transitions resulting in W to stop codon changes in the amino acid sequence at residues 323 and 511, respectively. The cDNA termination codon is marked with an asterisk. A sequence conforming to the consensus polyadenylation signal sequence is underlined, and sites of polyA attachment are marked in bold. Two independent cDNAs contained polyA fourteen nucleotides downstream of this signal; two alternative sites of attachment were also observed.

FIGS. 3A and 3B: Comparison of the sel-10, yeast CDC4 and mouse MD6 sequences.

Reverse contrast letters indicate amino acid identity between two of the three sequences. MD6 sequence (accession number X54352) and CDC4 sequence (accession number X05625) are from Genbank.

3A. Alignment of SEL-10 (SEQ ID NO: 3), CDC4 (SEQ ID NO: 4), and MD6 (SEQ ID NO: 5) F-Boxes.

3B. Alignment of WD40 repeats from SEL-10 (SEQ ID NO: 6) and CDC4 (SEQ ID NO: 7).

FIGS. 4A and 4B: Coimmunoprecipitation of murine Notch4(int3) and C. elegans SEL-10 from transfected 293T cells.

4A. Samples were immunoprecipitated with anti-Notch4 antibody and the Western blot was probed with anti-HA to visualize SEL-10HA (top panel) or anti-Notch4 to visualize Notch4(int3) (bottom panel).

4B. Samples were immunoprecipitated with anti-HA antibody and the Western blot was probed with anti-Notch4 (top panel) or anti-HA (bottom panel). For details see Experimental Procedures. Lane 1, mock transfected cells. Lane 2, pLNCint3+pQNCX. Lane 3, PLNCX+pQNCsel-10HA. Lane 4, pLNCint3+pQNCsel-10HA.

FIG. 5: SEL-10 lowers the steady-state level of Notch4 (int3).

Immunoblot analysis of Notch4(int3) proteins; the arrow indicates the expected mobility of Notch4(int3). Transient transfections of 293T cells were performed as described in Experimental Procedures. Lane 1, mock transfected cells (no DNA). Lane 2, pLNCint3+PQNCX. Lane 3, pLNCint3+ pQNCsel-10.

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

C=cytosine A=adenosine

T=thymidine G=guanosine

A "gene" means a nucleic acid molecule, the sequence of which includes all the information required for the normal regulated production of a particular protein, including the structural coding sequence, promoters and enhancers.

The nucleic acids or oligonucleotides of the subject invention also include nucleic acids or oligonucleotides coding for polypeptide analogs, fragments or derivatives which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These nucleic acids or oligonucleotides include: the incorporation of codons "preferred" for expression by selected non-mammalian or mammalian hosts; the provision of sites for cleavage by restriction endonuclease enzymes; and the provision of additional initial, terminal or intermediate DNA sequences that facilitate construction of readily expressed vectors.

The nucleic acids and oligonucleotides described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

This invention provides for an isolated nucleic acid which encodes SEL-10. This isolated nucleic acid may be DNA or RNA, specifically cDNA, synthetic DNA or RNA, or genomic DNA. This isolated nucleic acid also encodes mutant SEL-10 or the wildtype protein. Where the isolated nucleic acid encodes a mutated SEL-10, the mutation may be generated by in vitro mutagenesis. The isolated nucleic acid molecule encoding SEL-10 may have substantially the same amino acid sequence as shown in FIG. 2.

This isolated nucleic acid may also encode a polypeptide comprising the amino acid sequence of SEL-10.

As used in this application, "SEL-10" means and includes any polypeptide having SEL-10 activity, e.g. promotion of the turnover of mammalian Notch or mammalian presenilin. Thus, this term includes any such polypeptide whether naturally occurring and obtained by purification from natural sources or non-naturally occuring and obtained synthetically, e.g. by recombinant DNA procedures. Moreover, the term includes any such polypeptide whether its sequence is substantially the same as, or identical to the sequence of any mammalian homolog of the human polypeptide, e.g. murine, bovine, porcine, etc. homologs.

Additionally, the term includes mutants or other variants of any of the foregoing which retain at least some of the enzymatic activity of nonmutants or nonvariants.

The invention also encompasses DNAs and cDNAs which encode amino acid sequences which differ from SEL-10, but which do or do not produce phenotypic changes.

However, a mutant SEL-10 may not exhibit the same phenotype as the wildtype SEL-10. For example, a cell containing a mutant version of the sel-10 gene will express a protein unable to promote the degradation of mammalian Notch, or is able to better promote the degradation of mammalian Notch.

The nucleic acid of the subject invention also include nucleic acids that encode for polypeptide analogs, fragments or derivatives which differ from naturally-occurring forms in terms of the identity or location of one or more amino acid residues (including deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of the naturally-occuring forms.

The polypeptide of the subject invention also includes analogs, fragments or derivatives which differ from naturally-occurring forms, but retain SEL-10 activity.

This invention also provides an oligonucleotide of at least 15 nucleotides capable of specifically hybridizing with a unique sequence of nucleotides present within a nucleic acid which encodes a wildtype SEL-10 without hybridizing to a nucleic acid which encodes a mutant SEL- 10. These oligonucleotides may be DNA or RNA. Such oligonucleotides may be used in accordance with well known standard methods for known purposes, for example, to detect the presence in a sample of DNA which will hybridize thereto.

As used herein, "capable of specifically hybridizing" means wherein the oligonucleotide will selectively bind to only sequences which are unique to either nucleic acids encoding wildtype or mutant SEL-10.

The oligonucleotides include, but are not limited to, oligonucleotides that hybridize to mRNA encoding SEL-10 so as to prevent translation of the protein or cause RNA-mediated interference of endogenous gene expression.

This invention also provides a nucleic acid having a sequence complementary to the sequence of the isolated nucleic acid which encodes SEL-10.

This invention also provides a vector comprising an isolated nucleic acid encoding SEL-10. The isolated nucleic acid of the vectors is operatively linked to a promoter of RNA transcription which maybe, or is identical to, a bacterial, yeast, insect or mammalian promoter. The vector may be a plasmid, cosmid, yeast artificial chromosome (YAC), bacteriophage or eukaryotic viral DNA. Specifically, this invention provides for a plasmid designated psel-10.8/ 1A This specific embodiment, psel-10.8/1A made by cleaving DNA which encodes a wildtype *C. elegans* SEL-10 and inserting the DNA into a plasmid. psel-10.8/1A was deposited on July 22, 1997 with the American Type Culture Collection (ATCC), 12301 Parklawn Drive, Rockville, Md. 20852, U.S.A., under the provisions of the Budapest Treaty For The International Recognition Of The Deposit Of Microorganisms For The Purposes Of Patent Procedure. psel-10.8/1A has been accorded ATCC Accession Number 209154.

Further other numerous vector backbones known in the art as useful for expressing proteins may be employed. Such vectors include but are not limited to: adenovirus, simian virus 40 (SV40), cytomegalovirus (CMV), mouse mammary tumor virus (MMTV), Moloney murine leukemia virus, murine sarcoma virus, and Rous sarcoma virus, DNA delivery systems, i.e liposomes, and expression plasmid delivery systems.

This invention also provides a vector system for the production of a polypeptide which comprises the vector in a suitable host. Suitable host includes a cell which includes, but is not limited to, prokaryotic or eukaryotic cells, e.g. bacterial cells (including gram positive cells), yeast cells, fungal cells, insect cells and animal cells.

Suitable animal cells include, but are not limited to, HeLa cells, Cos cells, CV1 cells and various primary mammalian cells. Numerous mammalian cells may be used as hosts, including, but not limited to, the mouse fibroblast cell NIH 3T3, CHO cells, Ltk$^-$ cells, etc. Expression plasmids such as that described supra may be used to transfect mammalian cells by methods well known in the art such as calcium phosphate precipitation, electroporation.

This invention also provides a method for producing a polypeptide (e.g. SEL-10) which comprises growing a host vector system under suitable conditions permitting production of the polypeptide and recovering the polypeptide so produced. Methods of recovering polypeptides produced in such host vector systems are well-known in the art and typically include steps involving cell lysis, solubilization and chromatography. This invention also providies a method of obtaining a polypeptide in purified form which comprises: (a) introducing a vector, as described above, into a suitable host cell; (b) culturing the resulting cell so as to produce the polypeptide; (c) recovering the polypeptide produced in step (b); and (d) purifying the polypeptide so recovered. As discussed above the vector may include a plasmid, cosmid, yeast artificial chromosome, bacteriophage or eukaryotic viral DNA. Also, the host cell may be a bacterial cell (including gram positive cells), yeast cell, fungal cell, insect cell or animal cell. Suitable animals cells include, but are not limited to HeLa cells, Cos Cells, CV1 cells and various primary mammalian cells. Culturing methods useful for permitting transformed or transfected host cells to produce polypeptides are well known in the art as are the methods for recovering polypeptides from such cells and for purifying them.

Using the aforementioned method, this invention also provides a purified wildtype SEL-10 and purified fragments thereof, and a purified mutant SEL-10 and purified fragments thereof. Further, this invention also provides a polypeptide comprising the amino acid sequence of SEL-10, including, but limited to, fusion proteins having part of their amino acid sequence of the amino acid sequence of SEL-10.

Further, this invention provides where the SEL-10 produced is labeled. Different types of labeling exist. The labeling may be by various means. For instance one may tag the produced polypeptide with an established epitope such as myc. As discussed later in this application, such means of labeling are well known in the art. Further, one could also use other types of labels such as fluorescent, bioluminescent and metals.

This invention also provides a method for production of an antibody capable of binding to wild-type SEL-10 or mutated SEL-10 protein comprising: a) administering an amount of the purified protein or fragment of wild-type SEL-10 or mutated SEL-10 to a suitable animal effective to produce an antibody against wild-type SEL-10 or mutated SEL-10 protein in the animal; and b) testing the produced antibody for capability to bind wild-type SEL-10 or mutated SEL-10.

The antibody may be produced by in vitro immunization and tested by either Western blot analysis, immunoprecipitations, or staining of cells or tissue sections.

Antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

This invention also provides a method for production of an antibody capable of binding to wild-type SEL-10 or mutated SEL-10 protein comprising: a) determining conserved regions revealed by alignment of the wild-type SEL-10 or mutated SEL-10 protein sequences; b) synthesizing peptides corresponding to the revealed conserved regions; c) administering an amount of the synthesized peptides to a suitable animal effective to produce an antibody against the peptides in the animal; and d) testing the produced antibody for capability to bind wild-type SEL-10 or mutant SEL-10.

The antibody may be produced by in vitro immunization and tested by either Western blot analysis, immunoprecipitations, or staining of cells or tissue sections.

This invention also provides an antibody capable of specifically binding to wild-type SEL-10 or mutated SEL-10, and produced by the above-described methods. In a specific embodiment, the antibody is a monoclonal antibody. Further, the antibody may be labeled.

The labeled antibody may be a polyclonal or monoclonal antibody. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, radioactive or fluorescent. Methods of labeling antibodies are well known in the art.

This invention also provides transgenic animal comprising the isolated nucleic molecule encoding SEL-10, specifically the transgenic animal is a *Caenorhabditis elegans*.

This invention provides a method for identifying a compound which is capable of ameliorating Alzheimer's disease comprising administering an effective amount of the compound to the transgenic animal comprising the isolated nucleic acid molecule encoding SEL-10, alteration of the conditions of the transgenic animal indicating that the compound is capable of ameliorating Alzheimer's disease.

This invention also provides for a method for determining whether a compound is capable of ameliorating Alzheimer's disease comprising: a) treating *Caenorhabditis elegans* mutants having reduced, increased or altered sel-10 activity with the compound; and b) determining whether the compound suppresses, enhances or has no effect on the phenotype of the mutants, the suppression or enhancement of the phenotype indicating the compound is capable of ameliorating Alzheimer's disease. An alternative means of determination is by a) contacting the compound with a cell which expresses both SEL-12 and SEL-10; and b) determining whether the compound increases, decreases or has no effect on the amount of SEL-12 in the cell, the increase or decrease of SEL-12 indicating that the compound is capable of ameliorating Alzheimer's disease. A third means of determination is by contacting the compound with a cell which expresses both LIN-12 and SEL-10; and determining whether the compound increases, decreases or has no effect on the amount of LIN-12 in the cell, the increase or decrease of LIN-12 indicating that the compound is capable of ameliorating Alzheimer's disease. A fourth means for determining whether a compound is capable of ameliorating Alzheimer's disease comprising: a) contacting the compound with a cell which expresses both mammalian presenilin and SEL-10; and b)determining whether the compound increases, or decreases or has no effect on the amount of mammalian presenilin in the cell, the increase or decrease of mammalian presenilin indicating that the compound is capable of ameliorating Alzheimer's disease.

As used herein "LIN-12" is a homolog of mammalian Notch protein that is found in C. elegans.

As used herein "SEL-12" is a homolog of mammalian presenilin protein that is found in C. elegans.

This invention also provides a method for identifying a compound which is capable of treating cancer comprising administering an effective amount of the compound to the transgenic animal comprising the isolated nucleic acid encoding SEL-10, alteration of the conditions of the transgenic animal indicating that the compound is capable of treating cancer.

This invention provides also a method for determining whether a compound is capable of treating cancer comprising: a) treating Caenorhabditis elegans mutants having reduced, increased or altered sel-10 activity with the compound; and b) determining whether the compound suppresses, enhances or has no effect on the phenotype of the mutants, the suppression or enhancement of the phenotype indicating the compound is capable of treating cancer.

This invention also provides a method for determining whether a compound is capable of treating cancer comprising: a) contacting the compound with a cell which expresses both LIN-12 and SEL-10; and b) determining whether the compound increases, decreases or has no effect on the amount of LIN-12 in the cell, the increase or decrease of LIN-12 indicating that the compound is capable of treating cancer. Another means of determination is a) treating C. elegans mutants with the compound, b))determining whether the compound suppresses, enhances or has no effect on the phenotype of mutants, the suppression or enhancement of the phenotype indicating that the compound is capable of treating cancer. A third means of determination whether a compound is capable of treating cancer comprises a) contacting the compound with a cell which expresses both mammalian Notch and SEL-10; and b) determining whether the compound increases, decreases or has no effect on the amount of mammalian Notch in the cell, the increase or decrease of mammalian Notch indicating that the compound is capable of treating cancer.

This invention also provides a method for identifying a suppressor that affects lin-12 or sel-12 activity in the same manner as sel-10, comprising: a) mutagenizing lin-12 or sel-12 Caenorhabditis elegans worms with an effective amount of an appropriate mutagen: b) screening for revertants in the F1, F2, and F3 generations; and c) isolating the screened revertants, thereby identifying a suppressor of the phenotype of lin-12 or sel-12 mutation.

This invention also provides for a suppressor identified by the above-described method.

This invention also provides for a method for identifying an enhancer that affects lin-12 or sel-12 activity in the same manner as sel-10, comprising: a) mutagenizing lin-12 Caenorhabditis elegans worms with an effective amount of an appropriate mutagen; b)screening for enhancement in the F1, F2, and F3 generations; and c) isolating the screened enhancers, thereby identifying an enhancer of the phenotype of lin-12 or sel-12 mutation.

This invention also provides an enhancer identified by the above-described method.

This invention also provides a method for producing suppressors of a sel-10 allele comprising: a) mutagenizing sel-10 mutant hermaphrodites with an effective amount of a mutagen; b) screening for revertants in the F1, F2, and F3 generations; and c) isolating the screened revertants. This invention also provides a suppressor produced by the above-described method.

This invention also provides a method for identifying a suppressor gene comprising performing DNA sequence analysis of the suppressor identified by the above-described means to identify the suppressor gene, and the suppressor gene so identified.

This invention also provides a method for producing enhancers of a sel-10 allele comprising: a) mutagenizing sel-10 mutant hermaphrodites with an effective amount of a mutagen; b) screening for enhanced mutant in the F1, F2, and F3 generations; and c) isolating the screened enhancers. This invention also provides a enhanced mutant produced by the above-described method.

This invention also provides a method for identifying a enhancer gene comprising performing DNA sequence analysis of the enhancer identified by the above-described means to identify the enhancer gene, and the enhancer gene so identified.

This invention also provides a method for reversing the malignant phenotype of cells comprising: a) linking the wild-type or mutated sel-10 gene to a regulatory element such that the expression of the sel-10 gene is under the control of the regulatory element; and b) introducing the linked sel-10 gene into the malignant cells for the expression of the sel-10 gene so as to reverse the malignant phenotype of cells. One could place the cells from step (b) in appropriate conditions to express the sel-10 gene such that the expression of the sel-10 gene will reverse the transforming phenotype of the malignant cells.

In the above-described method, one could induce the expression of the sel-10 gene which will reverse the transforming properties of the cells, thereby reversing the phenotype of the malignant cells in the subject.

This invention also provides for pharmaceutical compositions comprising an effective amount of the compound identified to ameliorate Alzheimer's disease and a suitable carrier.

This invention also provides a pharmaceutical compositions comprising an effective amount of the compound identified to treat cancer and a suitable carrier.

Further one could ameliorate Alzheimer's disease by administrating the above-described pharmaceutical composition in an amount effective to ameliorate Alzheimer's disease.

One could also treat cancer by administering the above-described pharmaceutical composition in an amount effective to treat cancer.

This invention is illustrated in the Experimental Details section which follows. These sections are set forth to aid in an understanding of the invention but are not intended to, and should not be construed to, limit in any way the invention as set forth in the claims which follow thereafter.

Experimental Details
First Series Of Experiments
Experimental Procedures
1. General methods and strains General methods are described by Brenner (1974). The wild-type parent for all strains was C. elegans var. Bristol strain N2. Mapping experiments utilized the Bristol/Bergerac congenic strain GS352, in which the region between rol-4 and par-1 of Bristol was replaced with the corresponding region from the Bergerac strain BO (Tuck and Greenwald, 1996). Strains were grown at 20° unless otherwise noted.

Mutations used are described in Hodgkin (1997); additional references for critical alleles are also given.

LGIII: dpy-17(e164), unc-36(e251) andunc-32(e189) lin-12 (ar170) (Hubbard et al., 1996; E.J.A.H., unpublished observations); lin-12(n379) (Greenwald et al., 1983).

LGIV: dpy-20(e1282)

LGV: nDf42 (M. Hengartner and H. R. Horvitz, personal communication), lon-3(e2175) rol-4(sc8), sel-10(ar41) (Sundaram and Greenwald, 1993), him-5(e1490), unc-76 (e911).

2. Mapping of the sel-10 locus sel-10 had been genetically mapped between lin-25 and unc-76 V (Sundaram and Greenwald, 1993), and approximately 0.2 MU to the left of him-5. sel-10 was mapped between arP3 and TCPAR1 by identifying Rol Him non-Unc recombinants from heterozygotes of the genotype rol-4 BO unc-76/lon-3 sel-10 him-5 constructed using the strain GS352. Fifty independent recombinants were analyzed by Southern blot hybridization for the presence of arP3 and TCPAR1 (see Tuck and Greenwald, 1996), and each recombinant strain was tested for the presence of sel-10(ar4l) by crossing into lin-12(n379) and scoring for the Muv phenotype. Mapping data can be found in ACeDB (Edgley et al. 1997).

3. sel-10 cloning by anti-suppression assay sel-10(ar41) partially suppresses the 2AC defect caused by lin-12(ar170): at 25° C., ~80% of lin-12 (ar170) animals have 2AC while ~25% of lin-12(ar170); sel-10(ar41) animals have 2AC. Reversal of suppression was used as the basis of assessing sel-10(+) activity of microinjected DNAs. Transgenic lines were generated by microinjecting the germ lines of lin-12 (ar170); dpy-20(e1282);sel-10(ar41) him-5 (e1490) hermaphrodites with cosmid or plasmid DNA (Mello et al., 1991) at a concentration of 5 µg/ml, along with the dpy-20(+) transformation marker DNA at 10 µg/ml (plasmid pMH86; Han and Sternberg, 1991) and carrier Bluescript DNA (Stratagene) at 90 µg/ml. Synchronous populations were obtained by allowing groups of transgenic hermaphrodites to lay eggs at 20° C. for 1–2 hours and tranferring the eggs to 25° C. The non-Dpy L3 hermaphrodites were then scored for the number of anchor cells. The injected tester DNA was considered to contain sel-10(+) sequences if >50% of the non-Dpy animals had 2AC. Typically, 60–80% 2AC was achieved in these "rescued" lines. Arrays scored as having sel-10(+) activity were subjected to a second test, the ability to reverse the Muv phenotype of lin-12(n379);sel-10 (ar41). Initial rescue was obtained with a pool of seven overlapping cosmids from the region (each at 5 µg/ml), then with the single cosmid C07E11, and then with plasmids derived from C07E11, as shown in FIG. 1.

4. Plasmids containing sel-10 genomic sequences pJH151 was constructed by digesting cosmid C07E11 with BamHI and ligating the 15 kb fragment to Bluescript KS+ (Stratagene). pJH166 was constructed by ligating an 8kb PstI-SalI fragment from pJH151 into Bluescript KS+. The PstI site was from the vector, while the SalI site is from the genomic sequences. The ~9kb SalI fragment was removed from pJH151 to form pJH165, and pJH167 was made by ligation of the internal HindIII fragment of pJH151 into Bluescript. To construct pJH169, pJH166 was cut with PmeI and a linker containing an NheI site with a stop codon in all frames (NEB #1060) was inserted, creating a stop codon after amino acid 172 in the SEL-10 sequence.

5. sel-10 overexpression arEx93 was generated by microinjecting dpy-20 hermaphrodites with pJH166 [sel-10(+)] at a concentration of 100 µg/ml, pMH86 [dpy-20(+)] at 10 µg/ml, and Bluescript DNA at 90 µg/ml. Strains carrying this array segregate sterile animals as well as fertile animals; the basis for the sterility has not been established. Many of the fertile animals display a leaky Egl phenotype similar to that observed in certain lin-12 hypomorphic mutants. Similar results were observed with other lines at this concentration and with lines established using pJH166 at 50 µg/ml.

The control array arEx149 was established by microinjecting unc-32; dpy-20 hermaphrodites with pMH86 at 10 µg/ml, and Bluescript DNA at 90 µg/ml into unc-32; dpy-20 animals.

6. Molecular analysis of sel-10

Standard methods were used for the manipulation of recombinant DNA (Sambrook et al., 1989). sel-10(+) cDNAs were obtained by screening approximately 100,000 pfu from a phage library kindly provided by R. Barstead (Barstead and Waterston, 1989). Ten positive plaques were purified by two subsequent rounds of screening using a radiolabelled fragment from pJH166 (~8 kb BamHI/SalI fragment) as a probe. cDNA 1A, the longest cDNA obtained, was sequenced in its entirety on one strand and compared with genomic sequence from the genome project using GENEFINDER (see Waterston et al., 1997). The sequence of the cDNA 1A differed from the GENEFINDER prediction in the location of the junction between the second and third exons and in the predicted 3' end. Four of the cDNAs were polyadenylated at their 3' ends (one 294, one 581 and the other two 601 bases after the predicted stop codon). Of these, only the last two were in the context of a conserved polyadenylation signal. The 5'-most cDNA end was located in codon 1 (cDNA 8 begins at G of the first ATG), but a PCR product was amplified from DNA prepared from the same cDNA library (Barstead and Waterston, 1989; C. Dong, personal communication) contained the SL1 spliced leader at the predicted sequence 4 bases 5' of the first ATG. The 22 base SL1 sequence and a primer straddling the 5th and 6th exons were used for the 5' end amplification.

7. Sequence analysis

Standard techniques were used to obtain sequence of the 1A cDNA (Sambrook et al., 1989). The lesions associated with the sel-10(ar41) and sel-10(ar28) mutations were found by direct sequencing of two PCR products from single-stranded templates (Allard et al., 1991, Kaltenboeck et al., 1992), using internal primers to cover the entire region. One small segment was subcloned and sequenced (from two independent reactions each), as the sequence from this region was not easily generated using the direct method. Sequence comparisons and alignments were obtained using Blast (Altschul et al., 1990) through the NCBI web site and GCG (version 8, Devereux et al., 1984) programs.

8. Plasmids for cell culture experiments

Plasmids used in the transient transfection experiments were constructed in pLNCX (Miller et al., 1989) or PQNCX (Qingyou Yan and J. K., unpublished observations), vectors that drive gene expression under the control of a CMV promoter.

pLNCint-3 contains cDNA corresponding to the Notch4 region expressed in the int3 insertion, beginning at amino acid 1411. The Notch4(int3) protein includes the entire intracellular domain of Notch4 and additional sequences (see Uyttendaele et al., 1996).

pQNCsel-10HA (pJH184) encodes a protein with a methionine-containing hemagglutinin epitope from pACT2 (Durfee et al., 1993) fused in frame (along with a short stretch of polylinker) to cDNA 1A at amino acid 13.

pQNCsel-10 contains a cDNA beginning at position +3, and encodes a protein that is probably slightly truncated at the amino terminus, most likely beginning translation at the methionine codon 9 (+27). The normal termination codon is present.

9. Transfection and Western Blot Analysis 293T cells were maintained in DMEM with 10% fetal bovine serum (FBS). A confluent plate of cells was split 1:3 the day prior to transfection. For one 60 mm plate of cells, 4 µg of each plasmid DNA was transfected using the calcium phosphate precipitation method. The total amount of DNA was kept constant by supplementation with vector DNA.

Two days after transfection, cells were harvested and lysed in TENT buffer (50 mM Tris·Cl (pH 8.0), 2 mM EDTA, 150 mM NaCl, 1% Triton-X 100) containing protease inhibitors (2 µg/ml aprotinin, 2 µg/ml leupeptin, 2 µg/ml pepstatin, 0.5 mM PMSF). Lysates were clarified by centrifugation at 10,000 g for 10 min. and protein content was determined using the BioRad Protein determination kit. Lysates containing 60 kg protein were electrophoresed on 10% SDS-polyacrylamide gel and transferred onto nitrocellulose membrane. The blot was blocked overnight at 4° C. with TBST (10 mM Tris, pH 8.0, 150mM NaCl, 0.2% Tween 20) containing 1% Bovine serum albumin (TBST-BSA). The blot was then incubated with 1 antibody diluted (1:2,000 anti-Notch4; 1:50 for 12CA5) in TBST-BSA for 1 hour, washed three times for 5 minutes each with TBST, the blot was incubated with secondary antibody in TBST-ESA for 1 hour. After three washes, the signal was visualized by chemiluminescence (Amersham, ECL).

The anti-Notch4 antiserum (G. W. and J. K., unpublished observations) is directed against the C-terminal region of Notch4 (residues 1788-1964) (Uyttendaele et al., 1996). 12CA5 anti-HA antibody was obtained from Berkeley Antibody Co., Richmond, Calif.

10. Immunoprecipitation

Subconfluent 60-mm dishes of 293T cells were calcium-phosphate transfected with 8 mg of plasmid. Two days post-transfection, cell extracts were prepared by Triton X-100 lysis, as described above, and normalized for protein content. Extracts were precleared with sepharose CL-4B beads, incubated with antibodies (3 µl of anti-Notch4 antiserum or 50 µl of 9E10 supernatant) for six hours at 4_C, then incubated with 40 µl of 50% slurry of protein A-sepharose for 1 hour at 4° C. The protein A-sepharose beads were washed with TENT buffer three times by vortexing for 10 minutes, beads were boiled in 30 µl 1X protein loading buffer, and then electrophoresed on a 10% SDS-polyacrylamide gel and subjected to immunoblot analysis, as described above.

Results

Mutations that influence lin-12 activity in *C. elegans* may identify conserved factors that regulate the activity of lin-12/Notch proteins. We describe genetic evidence indicating that sel-10 is a negative regulator of lin-12/Notch mediated signalling in *C. elegans* are described. Sequence analysis shows that SEL-10 is a member of the CDC4 family. Biochemical data indicate that *C. elegans* SEL-10 physically interacts with LIN-12 and with murine Notch4, and that SEL-10 promotes LIN-12 and Notch4 degradation in mammalian cells. The parallel results obtained in *C. elegans* and mammalian cells suggest that negative regulation of lin-12/Notch activity by sel-10 is evolutionarily conserved. We discuss potential roles are discussed for the regulation of lin-12/Notch activity by sel-10 in cell fate decisions and tumorigenesis.

1. Lowering sel-10 dosage elevates lin-12 activity

Two sel-10 alleles, sel-10(ar28) and sel-10(ar4l), were identified in a screen for suppressors of defects caused by a partial loss-of-function allele of lin-12 (Sundaram and Greenwald, 1993). These sel-10 alleles were shown to suppress multiple defects associated with loss of lin-12 activity, and to enhance defects associated with elevated lin-12 activity (Sundaram and Greenwald, 1993). Here, evidence is provided that shows that sel-10 alleles reduce sel-10 activity, indicating that sel-10 is a negative regulator of lin-12 activity.

For the genetic analysis of sel-10, genetic interactions with mutations in lin-12 were relied upon. Two lin-12-mediated decisions were studied (reviewed in Greenwald, 1997). One decision is made by two cells of the hermaphrodite gonad, Z1.ppp and Z4.aaa, between the anchor cell (AC) and ventral uterine precursor cell (VU) fates; normally, only one of these two cells becomes the AC, while the other becomes a VU (see Introduction). Eliminating lin-12 activity causes both Z1.ppp and Z4.aaa to become ACs (the "2 AC defect"), and constitutively activating LIN-12 causes both Z1.ppp and Z4.aaa to become VUs. The other decision is made by the six vulval precursor cells, between a particular vulval fate termed "2°" or an alternative fate; normally, two of the six vulval precursor cells, P5.p and P7.p, adopt the 2° fate. Eliminating lin-12 activity causes all six vulval precursor cells to adopt alternative non-2° fates, and constitutively activating LIN-12 causes all six vulval precursor cells to adopt the 2° fate. Thus, mutants in which LIN-12 is constitutively active display a "0 AC Egg-laying (Egl) defect" because the absence of an AC prevents normal vulval formation; they are also Multivulva (Muv), because the descendants of each vulval precursor cell that adopts the 2° fate forms a pseudovulva.

To investigate the nature of the sel-10(ar41) allele, gene-dosage studies were performed assessing the enhancement of lin-12(n379), a weakly activated lin-12 allele in different sel-10 genetic backgrounds. lin-12(n379) homozygotes display the 0 AC-Egl defect, but do not have the Muv defect characteristic of strongly activated lin-12 alleles (Table 1, line 4). However, double mutants display a highly penetrant 0 AC-Egl phenotype and furthermore are Muv (Table 1, lines 1 and 2 and 4 and 7), suggesting that lin-12 activity is elevated by the sel-10(ar41) mutation.

TABLE 1 sel-10 gene dosage analysis.

| Relevant genotype | % Eql (n) | % Muv (n) | % Ste/Let (n) |
|---|---|---|---|
| 20* | | | |
| lin-12(d)/+[a] | 6 (93) | 0 (93) | 0 (93) |
| lin-12(d)/+;sel-10[b] | 91 (54) | 0 (54) | 0 (54) |
| lin-12(d)/+;sel-10/Df[c] | 92 (39) | 15 (39) | 0 (39) |
| 15* | | | |
| lin-12(d); +[d] | 86 (60) | 0 (60) | 0 (60) |
| lin-12(d);sel-10/+[e] | 98 (62) | 0 (62) | 0 (62) |
| lin-12(d);+/Df[f] | 89 (57)[i] | 62 (74) | 10 (63) |

TABLE 1-continued sel-10 gene dosage analysis.

| Relevant genotype | % Eql (n) | % Muv (n) | % Ste/Let (n) |
|---|---|---|---|
| lin-12(d);sel-10[g] | 100 (70)[i] | 78 (197) | 55 (126) |
| lin-12(d);sel-10/Df[h] | — | 85 (34) | 100 (34)[j] |

Complete genotypes are:
(a) lin-12(n379)/unc-36(e251); lon-3 (e2175)/him-5(e1490)
(b) lin-12(n379)/unc-36(e251); lon-3 (e2175) sel-10(ar41)
(c) lin-12(n379)/unc-36(e251); lon-3 (e2175) sel-10(ar41)/nDf42
(d) lin-12(n379); lon-3(e2175)/him-5(e1490)
(e) lin-12(n379); lon-3(e2175) sel-10(ar41)/him-5(e1490)
(f) lin-12(n379); lon-3(e2175) /nDf42
(g) lin-12(n379); lon-3(e2175) sel-10(ar41)
(h) lin-12(n379); lon-3(e2175) sel-10(ar41)/nDf42

The enhancement of the Muv defect of lin-12(n379)/+ hermaphrodites is more pronounced when sel-10(ar41) is placed in trans to the large deficiency nDf42 (Table 1, lines 2 and 3). The greater enhancement seen in trans to a deficiency may mean that the sel-10(ar41) allele is a partial loss of function allele rather than a null allele; alternatively, nDf42 may remove another gene that interacts with or is functionally redundant with sel-10.

Molecular data (see below) indicate that sel-10(ar41) would lead to a drastic truncation of the predicted SEL-10 protein, suggesting that sel-10(ar41) strongly reduces sel-10 activity.

Enhancment of the Muv defect of lin-12(n379) hermaphrodites was observed in nDf42/+ hermaphrodites (Table 1, lines 4 and 6). This result suggests that the sel-10 locus is haploinsufficient.

2. Elevating sel-10 dosage lowers lin-12 activity

The molecular cloning of sel-10(+) (see below) enabled examination of the effect of elevated sel-10(+) activity, since in general extrachromosomal arrays formed after injecting DNA at a high concentration result in higher transgene expression (Mello et al., 1991). Extrachromosomal arrays containing high-copy arrays of the sel-10 genomic region (see below) appear to lower lin-12 activity as assayed by their effect on the AC/VU decision. There is a dramatic decrease in the proportion of lin-12(n379) hermaphrodites displaying the 0 AC defect in the presence of the high copy number array arEx93 (Table 2A). In addition, the presence of the arEx93 array enhances the 2AC defect caused by a partial loss of lin-12 function (Table 2B) Therefore, the level of sel-10 activity appears to control the level of lin-12 activity, since increasing or decreasing the activity of sel-10 has reciprocal effects on lin-12 activity.

TABLES 2A and 2B

Increased dosage of sel-10 reduces lin-12 activity.

2A) Suppression of phenotypes associated with increased lin-12 activity

| Relevant genotype | % 0AC (n) |
|---|---|
| lin-12(d); dpy-20;Ex[sel-10(+) dpy-20(+)] | 51 (47) |
| lin-12(d); dpy-20;Ex[dpy-20(+)] | 95 (44) |

2B) enhancement of phenotypes asociated with reduced lin-12 activity

| Relevant genotype | % 2AC (n) |
|---|---|
| lin-12(h); dpy-20;Ex[sel-10(+) dpy-20(+)] | 97 (34) |
| lin-12(h); dpy-20;Ex[dpy-20(+)] | 30 (40) |
| lin-12(+);dpy-20(e1282);Ex[sel-10(+) dpy-20(+)] | 0 (0/87) |

3. Sel-10 Mutants Display Low Penetrance Defects Associated with Constitutive Activation of Lin-12

Most sel-10 animals appear wild-type. About 1% of sel-10(ar41) him-5 hermaphrodites were observed to lack an AC. Furthermore, about 4% of sel-10(ar41) males display a gonad Migration (Mig) defect similar to that seen in lin-12 (d) mutants, where it results from to failure to form the linker cell, the male counterpart of the hermaphrodite AC (Greenwald et al., 1983). In addition, about 8% of sel-10 mutant hermaphrodites are Egl even though they have an AC, and that sel-10 males have a reduced mating efficiency that can not be completely accounted for by the Mig defect. These additional defects may reflect the effect of increased lin-12 activity on other cell fate decisions (Greenwald et al., 1983).

4. Cell Autonomy of Sel-10 Function

Two lines of evidence suggest that sel-10 functions cell autonomously to elevate lin-12 activity. First, the effect of reducing sel-10 activity on the activity of the intracellular domain of LIN-12 was examined. Expression of lin-12 (intra) causes phenotypes associated with LIN-12 activation (Struhl et al., 1993). Since LIN-12(intra) lacks the extracellular domain and hence is active in the absence of external signalling, an enhancement of lin-12(intra) activity by sel-10 mutations would be evidence for cell autonomy of sel-10 function. An extrachromosomal array that contains the lin-12(intra) transgene and a transformation marker were used (see Experimental Procedures); this array results in a low-penetrance lin-12 activated phenotype (Table 3A).

TABLES 3A and 3B

Cell autonomy of sel-10 function.
3A) Enhancement of lin-12(intra)

| Relevant genotype | % Egl (n) | % Mig (n) |
|---|---|---|
| sel-10(+);arEx[lin-12(intra)] | 16 (88)[a] | 10 (57) |
| sel-10(ar41);arEx[lin-12(intra)] | 46 (136)[a] | 59 (90) |

All strains also contained him-5(e1490). arEx[lin-12(intra)]=arEx152 (Fitzgerald, personal communication) is an extrachromosomal array formed by microinjection (Fire, 1986; Mello et al., 1991) of pRF4 (plasmid containing rol-6(sul1006) sequence that confers a Rol phenotype onto worms carrying the array) at 100 μg/ml and pLC8 (Struhl et al., 1993).

[a]We infer that these Egl hermaphrodites lacked an AC because we scored additional hermaphrodites of relevant genotype sel-10; arEx[lin-12(intra)] in the L3 stage for the presence or absence of an AC and as adults for their egg-laying ability, and found that nine hermaphrodites that clearly had a single AC were non-Egl, while nine hermaphrodites that clearly lacked an AC were Egl.

3B) Cell Ablation

| | % 0AC (n) | |
|---|---|---|
| Relevant genotvpe | unoperated | operated |
| lin-12(n379)/+; sel-10(+) | 10 (57) | 9 (11) |
| lin-12(n379)/+; sel-10(ar41) | 97 (71) | 83 (12) |

When this array is combined with sel-10(ar41), there is a dramatic increase in the proportion of hermaphrodites displaying the 0 AC-Egl defect and males displaying the Mig defect (Table 3A), suggesting that sel-10 (+) activity normally reduces lin-12 function in the same cell.

sel-10 functions were tested in the receiving end of lin-12-mediated cell-cell interactions by performing cell ablation experiments to remove the signalling cell, in this case Z4.aaa (Table 3B). This experiment enables different genotypes to be compared with respect to their intrinsic level of constitutive lin-12 activity in Z1.ppp. If Z4, the precursor to Z4.aaa, is ablated in lin-12(n379)/+ hermaphrodites, Z1.ppp usually becomes an AC, because the level of constitutive lin-12 activity is relatively low. However, if Z4 is ablated in lin-12(n379)/+; sel-10 hermaphrodites, Z1.ppp usually becomes a VU, suggesting that the level of constitutive lin-12 activity is relatively high. These results suggest that sel-10 (+) functions to reduce lin-12 activity cell autonomously, since a high level of intrinsic lin-12 activity is seen when sel-10 activity is reduced even when the signalling cell is removed.

5. Cloning of Sel-10 by an Anti-Suppression Assay sel-10 was previously mapped to an interval between lin-25 and unc-76 on LGV (Sundaram and Greenwald, 1993). The map position to a 300 kb interval between the cloned polymorphisms arP3 and TCPAR1 space were refined (see Experimental Procedures and FIG. 1). Cosmids from the region were tested for their ability to reverse the suppression of the 2AC defect of lin-12(ar170) by sel-10 (ar41) (see Experimental Procedures). The cosmid C07E11 gave rescue in this anti-suppression assay and also reversed the enhancement of lin-12(n379) by sel-10 (ar41). This cosmid was further subcloned and the ~8 kb fragment in pJH166 gave results similar to that seen with the entire cosmid (FIG. 1).

6. Molecular Analysis of Sel-10

The ends of pJH166 (FIG. 1) were sequenced and compared with sequence generated by the *C. elegans* genome sequencing project (Waterson et al., 1997). The entire region was found on the cosmid F55B12. A fragment from the predicted open reading frame (genefinder) was radiolabeled and used to screen a Northern blot and to probe a cDNA library (see Experimental Procedures). Northern analysis revealed a single band of ~2.5kb which is present in total RNA prepared from wild type, sel-10(ar41) and sel-10(ar28) strains. The ends of ten cDNAs were sequenced and the largest cDNA was sequenced in its entirety on one strand. Verification of the 5' end was obtained by sequencing products amplified from the cDNA library using the trans spliced leader sequence SL1 (Krause and Hirsh, 1987) and a sel-10-specific sequence for primers. The splice junction of SL1 to the sel-10 coding region occurs four bases upstream of the first predicted start codon. FIG. 2 summarizes the results of the sequence analysis of sel-10.

7. Sel-10 Encodes a Protein of the Cdc4 Family of Proteins

A BLAST search (Altschul et al., 1990) using the predicted SEL-10 protein sequence revealed that it contains two previously identified amino acid sequence motifs (FIG. 3). There are seven tandem WD40 repeats, also known as βtransducin repeats, a conserved repeat of approximately 40 amino acids named for the common appearance of Trp-Asp (WD) at the end of the repeat (reviewed in Neer et al., 1994). The crystal structure of βtransducin reveals that the seven repeats form a 0 propeller structure, which most likely mediates protein-protein interactions (Gaudet et al., 1996; Lambright et al., 1996; Sondek et al., 1996). There is a great deal of functional diversity among WD40 repeat-containing proteins.

There is another motif (Kumar and Paitta, 1995) that is now called the F-Box, after its occurrence in cyclin F (Bai et al. 1996). The F-Box motif has also been implicated in protein-protein interactions, and is found in a large variety of proteins, many of which contain other recognizable motifs C-terminal to the F-Box (Bai et al., 1996).

The presence of an F box N-terminal to a set of seven WD40 motifs is the hallmark of the CDC4 family of WD40-repeat containing proteins, so SEL-10 appears to belong to this family. Furthermore, separate BLAST searches with just the SEL-10 WD40 repeats or the SEL-10 F box always identified members of the CDC4 family as the most similar. The alignment of the WD40 repeats of SEL-10 and CDC4 (FIG. 3B) reveals that a given WD40 repeat is more similar between yeast and worms than are the repeats within a given species. In addition, the F-Box motif present in proteins within the CDC4 subfamily is more conserved than among other F-Box-containing proteins (FIG. 3A), and there is more extensive homology around the F-box (Kumar and Paitta, 1995).

The CDC4 family includes proteins in fungi and vertebrates, as well as two other predicted *C. elegans* proteins (see Discussion). The best studied member of this family, *S. cerivisiae* CDC4 targets Sic1 and certain G1 cyclins for degradation (reviewed in King et al., 1996). However, not all CDC4 family members are cell cycle regulators. For example, there are proteins that negatively regulate sulfur metabolism from *S. cerevisiae, Neurospora crassa* and *Aspergillis nidulans* (Natorff et al., 1993; Kumar and Paietta, 1995; Thomas et al., 1995). Biochemical mechanisms for other CDC4 family members have not been described.

8. Sel-10 Mutations Truncate the SEL-10 Protein

Sequence analysis of sel-10 mutations supports the genetic evidence suggesting that they strongly reduce sel-10 activity. The sequence alterations caused by sel-10(ar41) and sel-10(ar28) were determined by direct sequencing of amplified genomic DNA products (see Experimental Procedures). Both alleles are nonsense mutations at nucleotide positions 969 and 1533, respectively (see FIG. 2), resulting in truncated predicted proteins.

Sel-10(ar41) removes the C terminal half of the protein, including five of the seven WD40 repeats. This observation suggests that sel-10(ar41) is likely to result in a nonfunctional SEL-10 protein. It is unlikely that the two WD40 repeats that remain in this protein are functional since there are no known WD40-repeat containing proteins with only two repeats (Neer et al., 1994). Furthermore, the crystal structure of β transducin reveals that the seven repeats form a β propeller structure that would not be complete in the absence of five of the seven repeats (Sondek, et al., 1996). Finally, comparable mutations in another *C. elegans* CDC4 subfamily protein, LIN-23, behave like molecular null alleles (Kipreos, et al., submitted).

9. *C. elegans* SEL-10 Physically Interacts with LIN-12 (intra) and Murine Notch4(int3)

The observations that sel-10 negatively regulates lin-12 activity and resembles CDC4 suggested the possibility that SEL-10 functions biochemically like CDC4 to promote LIN-12 turnover. This model makes two predictions. First, SEL-10 should physically interact with LIN-12/Notch proteins. Second, the steady-state level of LIN-12/Notch proteins should be reduced by expression of SEL-10.

Potential interactions between SEL-10 and the intracellular domains of LIN-12/Notch proteins were probed, specifically LIN-12(intra), the intact intracellular domain (see Struhl et al., 1993) and Notch4(int3), the intact intracellular domain with some additional sequences produced by the int3 mutation (Robbins et al., 1992; Uyttendaele et al., 1996).

Initially the yeast two-hybrid system (Fields and Song, 1989) was used and preliminary results suggested that SEL-10 physically interacted with the *C. elegans* LIN-12 and GLP-1 intracellular domains, and the mouse Notch4 (int3) intracellular domain. To examine further whether SEL-10 binds LIN-12/Notch proteins in vivo, co-immunoprecipitation experiments using transfected mammalian cells were carrried out (FIG. 4). 293T (Bosc) cells (human embryonic kidney cells) were transiently transfected with Notch4(int3) and/or HA-tagged SEL-10. Transfected cells were lysed and Notch4(int-3) was precipitated with anti-Notch4 antibodies or, alternatively, SEL-10HA was immunoprecipitated with anti-HA antibodies. The immunoprecipitates were subjected to immunoblot analysis to identify bound proteins, and probed with anti-HA and anti-Notch4 antibodies. Under both conditions, the immunoprecipitates were found to contain both Notch4(int3) and SEL-10HA. Similar results were obtained using Myc-tagged SEL-10. It was concluded that SEL-10 can be found in a complex with Notch4 in vivo.

Similar experiments were performed with epitope-tagged LIN-12(intra), and the coimmunoprecipitation results suggested that LIN-12 and SEL-10 also physically interact (data not shown). However, LIN-12 (intra) was poorly expressed in mammalian cells, so we proceeded with our analysis using Notch4(int3) exclusively.

10. *C. elegans* SEL-10 Reduces the Steady State Levels of Murine Notch4(int3)

If SEL-10 functions similarly to CDC4 in targeting specific proteins for proteolysis, then expression of SEL-10 might reduce the level of LIN-12/Notch proteins. The effect of expressing SEL-10 on the steady state levels of Notch4 (int3) was examined.

Transient transfection experiments in 293T cells were performed, in which the steady state level of Notch4(int3) was examined in the presence or absence of SEL-10. Western blot analysis revealed that the steady state level of Notch4(int3) is reduced in cells expressing SEL-10 as compared to mock transfected cells (FIG. 5a). Three independent transient transfection experiments performed in this manner yielded comparable results. A reduction in the steady state level of Notch4(int3) when epitope-tagged forms of SEL-10 were used in transient transfection experiments were also usually observed. In the co-immunoprecipitation experiments described above, less Notch4(int3) precipitated from cells were consistently seen that also contained transfected SEL-10, consistent with a reduced steady-state level of Notch4(int3) protein in the presence of SEL-10 (see FIG. 4).

The results suggest that the biochemical mechanism by which sel-10 functions as a negative regulator of lin-12/ Notch activity is by promoting LIN-12/Notch degradation. Applicants were unable to look directly at whether SEL-10 promotes ubiquitination of Notch4(int3) because there is substantial polyubiquitination of Notch4(int3) even in the absence of transfected SEL-10. The fact that the effects we see in this transfection system are relatively modest, and that ubiquitination occurs even in the absence of transfected SEL-10, may be due to the activity of an endogenous murine sel-10-like gene.

Discussion

In this paper, gelletic evidence indicates that sel-10 is a negative regulator of lin-12 mediated signalling in *C. elegans*. Mutations that lower sel-10 activity elevate lin-12 activity, and increasing sel-10 dosage lowers lin-12 activity. Furthermore, sel-10 appears to act in the same cell as lin-12.

Molecular and biochemical evidence suggest that the mechanism by which sel-10 controls lin-12 activity is by controlling LIN-12/Notch protein levels. First, sequence analysis indicates that SEL-10 is related to the Saccharomyces cerevisiae protein CDC4, which is involved in the ubiquitin-dependent degradation of cell cycle regulators (reviewed in King et al., 1996). Second, *C. elegans* SEL-10 physically interacts with the intracellular domain of LIN-12 and with Notch4(int3), the intracellular domain of murine Notch4. Third, coexpression of SEL-10 with Notch4(int3) causes a reduction in the steady-state level of Notch4(int3).

The effects of sel-10 activity on lin-12 in *C. elegans* and the effect of SEL-10 expression on Notch4 stability in culture are strikingly parallel. Furthermore, *C. elegans* SEL-10 interacts physically with murine Notch 4, and proteins related to SEL-10 exist in mammals. These observations suggest that the negative regulation of LIN-12/Notch by SEL-10 is an evolutionarily conserved feature. Evidence suggests that SEL-10 targets LIN-12/Notch proteins for degradation. Also, potential roles for protein turnover in LIN-12/Notch-mediated cell fate decisions were considered.

1. SEL-10 May Target LIN-12/Notch Proteins for Ubiquitin-Mediated Degradation

The attachment of ubiquitin to substrates involved a series of protein complexes. Ubiquitin is activated by linkage to an E1 ubiquitin activating enzyme, then transferred to an E2 ubiquitin conjugating enzyme. Some ubiquitination events also require the action of a third complex, termed E3. It is thought that E3 complexes may contribute to substrate specificity (reviewed in Ciechanover, 1994; King et al., 1996). The Saccharomyces cerevisiae protein Cdc4p may function in an E3 complex. CDC4 is one of a group of genes that also includes CDC34, CDC53, and SKP1; together, these genes directly regulate the level of the cyclin dependent kinase inhibitor Sic1p, which must be destroyed for progression from G1 to S phase. Cdc34p is an E2 ubiquitin conjugating enzyme (Goebl et al., 1988), and the current view is that Cdc4p, Cdc53p, and Skp1p function as an E3 complex (Bai et al., 1996; Mathias et al., 1996). Based on analysis of sel-10 and the data for CDC4, SEL-10 may function as part of an E3 complex to target the intracellular domains of LIN-12/Notch proteins for ubiquitin-dependent degradation.

An important issue to consider in the context of SEL-10 as a component of an E3 complex is its specificity for LIN-12/Notch proteins. The available *C. elegans* genetic data suggest that sel-10 an allele-nonspecific, gene-specific suppressor, supporting a role for SEL-10 specifically in regulating the activity of LIN-12, or perhaps a small subset of proteins that includes LIN-12. Allele-nonspecificity is indicated by the observation that mutations in sel-10 suppress/enhance all lin-12 alleles tested (Sundaram and Greenwald, 1993b; this work; E.J.A.H., unpublished observations). Gene-specificity is suggested by the fact that mutations in sel-10 have not been identified in numerous screens in many laboratories for suppressors of other hypomorphic mutations; furthermore, suppression of various marker mutations usied in routine strain constructions of hypomorphic alleles of several other genes encoding receptor proteins unpublished observations).

The available genetic data also suggest that sel-10 activity is not necessary for cell cycle progression, a possibility raised by the phenotype of cdc4 mutants. Mutations in cul-1, a *C. elegans* gene related to *S. cerevisiae* CDC53, cause hyperplasia of larval blast cells, suggesting that cul-1 regulates cell-cycle progression (see Kipreos et al., 1996). No evidence that hyperplasia occurs in sel-10(ar41) mutants has been seen. (E.J.A.H., unpublished observations). Since sel-10(ar41) mutants have little or no sel-10 activity (see Results), it is unlikely that sel-10 is involved in cell cycle regulation per se, unless there is another functionally redundant gene that masks cell cycle involvement of sel-10. In contrast, mutations in another CDC4 related gene, lin-23, do cause hyperplasia, consistent with a role for lin-23 in the regulation of cell cycle progression (Kipreos et al., submitted).

2. SEL-10 Mediated Degradation of LIN-12/Notch as a Mechanism for Receptor Downregulation For a variety of cell surface receptors, ligand-induced polyubiquitination is thought to be a mechanism for down-regulation (reviewed in Ciechanover and Schwartz, 1994). It is proposed that ubiquitin-mediated degradation is also a mechanism for down-regulation of activated LIN-12/Notch proteins, and that SEL-10 plays a critical role in this process. Although no direct evidence exists for ligand-induced ubiquitination of LIN-12/Notch receptors, the free and intact intracellular domains of LIN-12/Notch proteins have been shown to behave like activated receptors (Lieber et al., 1993; Struhl et al., 1993), and that Notch4(int3) behaves like a gain-of-function mutation (Gallahan and Callahan, 1987). Biochemical data are therefore consistent with the proposal that the activated receptor may be the substrate for SEL-10-mediated polyubiquitination. For the remainder of the Discussion, possible roles of SEL-10 mediated down-regulation of LIN-12/Notch proteins in cell fate decisions and oncogenesis are considered.

3. Potential roles for SEL-10 mediated LIN-12 down-regulation in the AC/VU decision and VPC specification sel-10 influences lin-12 activity in the AC/VU decision. The AC/VU decision can be considered to involve three phases prior to the committed state (Seydoux and Greenwald, 1989; Wilkinson et al., 1994). Initially, Z1.ppp and Z4.aaa have equal signalling and receiving potentials; ligand (LAG-2) and receptor (LIN-12) may interact, but signalling activity is below a critical threshold. A small stochastic difference between the two cells, such that one cell has a greater level of signalling activity and the other has a greater level of receiving activity, is amplified by a feedback mechanism that involves differential transcription of ligand and receptor genes. This feedback mechanism amplifies the stochastic difference that has arisen between the two cells and ensures that the cell in which lin-12 activity is greater becomes the VU while the cell in which lin-12 activity is less becomes the AC.

The ultimate consequences of LIN-12 activation must be on gene expression. For the feedback mechanism, this effect has been visualized for the transcription of lag-2 and lin-12: activation of LIN-12 appears to repress transcription of lag-2 and stimulate transcription of lin-12 (Wilkinson et al., 1994). At a minimum, downstream genes needed for differentiation as a VU must be activated; it is also likely that genes involved in the differentiation of an AC are repressed. sel-10 might influence the AC/VU decision because, unless LIN-12 is down-regulated, the initial signalling that occurs between Z1.ppp and Z4.aaa might cause both cells to achieve the threshold value of effector activity.

Most sel-10(ar41) individuals are phenotypically wild-type, with only a small proportion displaying phenotypes associated with LIN-12 activation, may be explained in this context if there is a redundant gene product or regulatory mechanism. There is at least one additional CDC4 related gene in the C. elegans genome (E.J.A.H., unpublished observations). Furthermore, there may be other mechanisms for degrading activated LIN-12. For example, sel-1, another negative regulator of lin-12 activity, may also be involved in LIN-12 turnover (see Grant and Greenwald, 1997), but since SEL-1 is a secreted or extracytosolic membrane-associated protein found in intracellular vesicles, it is not likely to be directly involved in the ubiquitination of the intracellular domain of LIN-12.

4. Potential Roles for Degradation of Activated LIN-12/Notch Proteins in Other Cell Fate Decisions In other cell fate decisions, including specification of the vulval precursor cells (VPCs), the role of sel-10 in the VPC decions may be similar to its role in the AC/VU decision: to ensure that a threshold value of LIN-12 activiniation must be reached in the appropriate cells for commitment. However, regulated turnover of activated receptors may play different or additional roles in other LIN-12/Notch mediated decisions. For example, in Drosophila eye development, Notch appears to be utilized for sequential cell fate decisions (Cagan and Ready, 1989), which would seem to necessitate clearance of activated Notch after each decision so that a new assessment of Notch activity can be made. Furthermore, it is also conceivable that for some LIN-12/Notch mediated decisions, the cell fate adopted may depend on the intensity of signal, as has been seen for receptors for gradient morphogens (e.g., Nellen et al., 1996). If any LIN-12/Notch-mediated decisions do display such dosage sensitivity, it is likely that they would depend on rapid turnover of activated receptor complexes so that the correct threshold value is read.

5. Potential Roles for sel-10 in Oncogenesis

When the intact intracellular domain of LIN-12/Notch proteins is expressed, cell fate transformations known to be associated with activation of LIN-12/Notch proteins are seen, indicating that the intact intracellular domain behaves like a constitutively active receptor (Lieber et al., 1993; Struhl et al., 1993). Thus, the observation that mammalian tumors can be induced by expression of truncated forms of Notch largely consisting of the intact intracellular domain (Ellisen et al., 1991; Robbins et al., 1992; Uyttendaele et al., 1996) suggests that constitutive Notch activity can be a causal factor in tumor formation. Since SEL-10 downregulates Notch activity, it may act to restrain the either normal or oncogenic functions of activated Notch, and hence suppress cell growth. If so, then loss-of-function mutations in vertebrate sel-10 could contribute to tumor formation by elevating the level of Notch protein. For instance, human T acute lymphoblastic leukemias, which in the majority of cases do not contain oncogenic Notch alterations (Drexler et al., 1995), and human breast tumors, which thus far have not been reported to contain oncogenic Notch alterations, may carry mutations in other proteins that influence Notch activity, such as sel-10 homologs.

Second Series of Experiments

1. Genetic Interaction Between sel-10 and sel-12 sel-12(ar171) and sel-12(ar131) cause an egg-laying defective (Egl) phenotype. sel-10(ar41) suppresses the Egl defect of sel-12 mutants (Table 4).

TABLE 4

All strains also contained the markers
him-5(e1490), and unc-1(e538).

| Relevant genotype | #Egl+/total (%) |
|---|---|
| sel-10(+); sel-12(ar131) | 2/99 (2%) |
| sel-10(ar41); sel-12(ar131) | 88/118 (75%) |
| sel-10(+); sel-12(ar171) | 0/107 (0%) |
| sel-10(ar41) sel-12(ar171) | 25/126 (20%) |

2. Potential physical interaction between SEL-10 and SEL-12, and SEL-10 and human presenilin 1 (PSi)

The genetic interaction between sel-10 and sel-12 raises the possibility that there is a direct physical interaction between the SEL-10 and SEL-12 proteins that promotes the ubiquitin-mediated turnover of SEL-12 presenilin. Experiments similar to those described in the first series of experiments, substituting SEL-12 in place of LIN-12, can be performed. Specifically, co-immunoprecipitation of epitope-tagged forms of SEL-10 and SEL-12, can be performed lowering of steady-state levels of SEL-12 in the presence of SEL-10, and ubiquitination of SEL-12 in the presence of SEL-10 will be observed. Similar experiments with human PS1, other human presenilins (e.g. PS2) and other *C. elegans* presenilins (HOP-1) can be performed. The genetic interactions of SEL-10 and other *C. elegans* presenilins will also be performed.

3. Implications for Alzheimer's disease

If there is a physical interaction between SEL-10 and SEL-12, such that SEL-10 promotes the ubiquitin-mediated degradation of SEL-12, then compounds that interfere with this process will be potential drugs for Alzheimer's disease.

If there is no direct physical interaction between SEL-10 and SEL-12, then the suppression of sel-12 mutations by sel-10 mutations is indirect, perhaps through effects on LIN-12. However, given the intimate connection between LIN-12/Notch and SEL-12/presenilin in *C. elegans* (Levitan and Greenwald, 1995) and mice (Wong et al., 1997; Shen et al., 1997), then compounds that interfere with the degradation of LIN-12 will be potential drugs for Alzheimer's disease.

4. sel-10 as a starting point for screens for other potential targets

A) Yeast two-hybrid screen for proteins that interact with SEL-10.

The two-hybrid screen, originally developed by Fields and Song (1989), is a powerful strategy for identifying potential interacting proteins. The screen relies on the ability of GAL4 to activate transcription of a reporter gene containing GAL4 upstream activation sequences. GAL 4 has a DNA binding domain (GBD) and a activation domain (GAD). Normally, the two domains are present in the same polypeptide; if they are separated, GAL4 activity is abolished. However, if the separated domains are joined to protein sequences that interact with each other, the two domains are brought together, and GAL4 activity is restored. Thus, a yeast strain containing a "bait" fused to the GBD is transformed with a library containing potential GAD fusions, and a selection or screen for reconstituted GAL4 activity is used to identify candidates.

This method to identify genes that interact with lin-12 (Hubbard et al., 1996) has been used. A similar approach to identifying genes that interact with sel-10 will be used. A bait containing sequences from SEL-10 fused to GBD has been prepared, and a derivative of yeast strain Y153 with this plasmid will be prepared. Y153 contains GAL4 UAS—HIS3 and GAL 4 UAS—lacZ, enabling candidates to be selected by the ability to grow on medium containing 3AT (HIS+ selection) or screened for beta-galactosidase activity (Durfee et al., 1993). Clones of the excellent random oligomer-primed library prepared by Bob Barstead by transforming the yeast strain Y153 and selecting for growth on 3AT plates will be screened; these transformants for beta-galactosidase activity will be screened in a filter assay. Then, from each candidate, the candidate worm-GAD plasmid will be isolated and retested with the bait (SEL-10-GBD), and with SNF1-GBD and/or lamin-GBD to check for general stickiness.

Any candidates that specifically bind SEL-10-GBD will be isolated and sequenced. The sequence analysis and derived map position (using the genome project database) may help illuminate their functions. To see if the physical interaction is functionally relevant in vivo, *C. elegans* mutants will be created by RNA interference or gene-knockout strategies using established methods. The candidate mutants for phenotypes and for genetic interactions with existing sel-12, sel-10, and lin-12 mutants will then be examined.

B) Genetic screens for mutations that interact with sel-10 will be conducted, specifically looking for extragenic suppressors or enhancers.

Screens that may be used are:

1) Mutagenizing appropriate strains so as to generate hermaphrodites of relevant genotype lin-12(n379); sel-10/Df (sel-10); * [where * represents a mutagenized chromosome] and look for fertile hermaphrodites. These individuals may carry extragenic suppressors that define new components of the sel-10 pathway or complex. Genetic and molecular characterization of extragenic suppressors of sel-10, including their interaction with mutations in sel-12 and lin-12, may identify other potential targets for drugs against Alzheimer's disease and cancer, other potential tumor suppressors or oncogenes that act in the lin-12 pathway, and other potential genes influencing the development of Alzheimer's disease.

2) Mutagenizing appropriate strains so as to generate hermaphrodites of relevant genotype arEx93 [sel-10(+)]; * to revert the sterility defect associated with sel-10 overexpression. Other high copy number or highly expressing arrays in place of arEx93 may also be used. As described above, these individuals may carry extragenic suppressors that define new components of the sel-10 pathway or complex. Genetic and molecular characterization of extragenic suppressors of sel-10, including their interaction with mutations in sel-12 and lin-12, may identify other potential targets for drugs against Alzheimer's disease and cancer, other potential tumor suppressors or oncogenes that act in the lin-12 pathway, and other potential genes influencing the development of Alzheimer's disease.

REFERENCES

1. Altschul, S. F., W. Gish, W. Miller, E. W. Meyers, and D. J. Lipman (1990). Basic local alignment search tool. J. Mol. Biol. 215, 403–410.
2. Aroian, R. V., M. Koga, J. E. Mendel, Y. Ohshima, and P. W. Sternberg (1990). The let-23 gene necessary for *Caenorhabditis elegans* vulval induction encodes a tyrosine kinase of the EGF receptor subfamily. Nature 348, 693–9.
3. Artavanis-Tsakonas, S., K. Matsuno, and M. E. Fortini (1995). Notch signaling. Science 268, 225–235.
4. Bai, C., P. Sen, K. Hofmann, L. Ma, M. Goebl, J. W. Harper, and S. J. Elledge (1996). SKP1 connects cell cycle regulators to the ubiquitin proteolysis machinery through a novel motif, the F-box. Cell 86, 263–274.
5. Barstead, R. J., and R. H. Waterston (1989). The basal component of the nematode dense-body is vinculin. J. Biol. Chem. 264, 10177–10185.
6. Brenner, S. (1974). The genetics of *Caenorhabditis elegans*. Genetics 77, 71–94.
7. Cagan, R. L., and D. F. Ready (1989). Notch is required for successive cell decisions in the developing Drosophila retina. Genes Dev. 3, 1099–1112.
8. Chitnis, A., D. Henrique, J. Lewis, D. Ish-Horowicz, and C. Kintner (1995). Primary neurogenesis in Xenopus embryos regulated by a homolog of the Drosophila neurogenic gene Delta. Nature 375, 761–766.
9. Christensen, S., V. Kodoyianni, M. Bosenberg, L. Friedman, and J. Kimble (1996). lag-1, a gene required for lin-12 and glp-1 signaling in *C. elegans*, is homologous to human CBF1 and Drosophila Su(H). Development 122, 1373–1383.
10. Ciechanover, A. (1994). The ubiquitin-proteasome proteolytic pathway. Cell 79, 13–21.
11. Ciechanover, A., and A. L. Schwartz (1994). The ubiquitin-mediated proteolytic pathway: mechanisms of recognition of the proteolytic substrate and involvement in the degradation of native cellular proteins. FASEB J. 8, 182–191.
12. Devereux, J., P. Haeberli, and O. Smithies (1984). A comprehensive set of sequence analysis programs for the VAX. Nucl. Acids Res. 12, 387–395.
13. DeVore, D. L., H. R. Horvitz, and M. J. Stern (1995). An FGF receptor signaling pathway is required for the normal cell migrations of the sex myoblasts in *C. elegans* hermaphrodites. Cell 83, 611–620.
14. Drexler, H. G., MacLeod, R. A. F., Borkhardt, A. and Janssen, J. W. G. (1995). Recurrent chromosomal translocations and fusion genes in leukemia-lymphoma cell lines. Leukemia 9, 480–500.
15. Durfee, T., Becherer, K., Chen, P. -L., Yeh, S. -H., Kilburn, A. E., Lee, W. -H. and Elledge, S. J. (1993) The retinoblastoma protein associates with the protein phosphatase type 1 catalytic subunit. Genes Dev. 7, 1–12.
16. Edgley, M. L., Turner, C. A., and Riddle, D. L. (1997) On-line *C. elegans* resources. In *C. elegans* II, D. L. Riddle, T. Blumenthal, B. J. Meyer and J. R. Priess, eds. (Cold Spring Harbor Laboratory Press), 1059–1062.
17. Ellisen, L. W., J. Bird, D. C. West, A. L. Soreng, T. C. Reynolds, S. D. Smith, and J. Sklar (1991). TAN-1, the human homolog of the Drosophila Notch gene, is broken by chromosomal translocations in T lymphoblastic neoplasms. Cell 66, 649–661.
18. Fields, S., and O. -k. Song (1989). A novel genetic system to detect protein-protein interactions. Nature 340, 245–246.
19. Gallahan, D., and R. Callahan (1987). Mammary tumorigenesis in feral mice: identification of a new int locus in mouse mammary tumor virus (Czech II)-induced mammary tumors. J. Virol. 61, 66–74.
20. Gaudet, R., A. Bohm, and P. B. Sigler (1996). Crystal structure at 2.4 A resolution of the complex of transducin bg and its regulator, phosducin. Cell 87, 577-568.
21. Grant, B., and I. Greenwald (1997). Structure, function and expression of SEL-1, a negative regulator of LIN-12 and GLP-1 in *C. elegans*. Development 124, 637–644.
22. Greenwald, I. (1997). Development of the vulva. In *C. elegans* II, D. L. Riddle, T. Blumenthal, B. J. Meyer and J. R. Priess, eds. (Cold Spring Harbor Laboratory Press), 519–542.
23. Greenwald, I., and G. Seydoux (1990). Analysis of gain-of-function mutations of the lin-12 gene of *Caenorhabditis elegans*. Nature 346, 197–9.
24. Greenwald, I. S., P. W. Sternberg, and H. R. Horvitz (1983). The lin-12 locus specifies cell fates in *Caenorhabditis elegans*. Cell 34, 435–444.
25. Han, M., and P. W. Sternberg (1991). Analysis of dominant-negative mutations of the *Caenorhabditis elegans* let-60 ras gene. Genes & Dev. 5, 2188–98.
26. Heitzler, P., and P. Simpson (1991). The choice of cell fate in the epidermis of Drosophila. Cell 64, 1083–1092.
27. Hodgkin, J. (1997) Genetics. In *C. elegans* II, D. L. Riddle, T. Blumenthal, B. J. Meyer and J. R. Priess, eds. (Cold Spring Harbor Laboratory Press), 881–1047.
28. Hubbard, E. J. A., Dong, Q., and Greenwald, I. (1996) Evidence for physical and functional association between EMB-5 and LIN-12 in *Caenorhabditis elegans*. Science 273, 112–115.
29. Kimble, J. (1981). Alteration in cell lineage following laser ablation of cells in the somatic gonad of *Caenorhabditis elegans*. Dev. Biol. 87, 286–300.
30. Kimble, J., and D. Hirsh (1979). The post-embryonic cell lineages of the hermaphrodites and male gonads in *Caenorhabditis elegans*. Dev. Biol. 87, 396–417.
31. King, R. W., R. J. Deshaies, J. -M. Peteres, and M. W. Kirschner (1996). How proteolysis drives the cell cycle. Science 274, 1652–1658.
32. Kipreos, E. T., L. E. Lander, J. P. Wing, W. W. He, and E. M. Hedgecock (1996). cul-1 is required for cell cycle exit in *C. elegans* and identifies a novel gene family. Cell 85, 829–839.
33. Krause, M. and D. Hirsh (1987). A trans-spliced leader sequence on actin mRNA in *C. elegans*. Cell 49, 753–761.
34. Kumar, A., and J. V. Paietta (1995). The sulfur controller-2 negative regulatory gene of *Neurospora crassa* encodes a protein with beta-transducin repeats. Proc. Natl. Acad. Sci. (USA) 92, 3343–3347.
35. Lambright, D. G., J. Sondek, A. Bohm, N. P. Skiba, H. E. Hamm, and P. B. Sigler (1996). The 2.0 A crystal structure of a heterotrimeric G protein. Nature 379, 311–319.
36. Lieber, T., S. Kidd, E. Alcamo, V. Corbin, and M. W. Young (1993). Antineurogenic phenotypes induced by truncated Notch proteins indicate a role in signal transduction and may point to a novel function for Notch in nuclei. Genes Dev. 7, 1949–1965.
37. Mango, S. E., E. M. Maine, and J. Kimble (1991). Carboxy-terminal truncation activates glp-1 protein to specify vulval fates in *Caenorhabditis elegans*. Nature 352, 811–815.
38. Mathias, N., S. L. Johnson, M. Winey, A. E. M. Adams, L. Goetsch, J. R. Pringle, B. Byers, and M. G. Goebl (1996). Cdc53p acts in concert with Cdc4p and Cdc34p to control the G1-to-S phase transition and identifies a conserved family of proteins. Mol. Cell Biol. 16, 6634–6643.
39. Mello, C. C., J. M. Kramer, D. Stinchcomb, and V. Ambros (1991). Efficient gene transfer in *C. elegans*: extrachromosomal maintenance and integration of transforming sequences. EMBO J. 10, 3959–3970.
40. Miller, A. D. and Rosman, G. J. (1989). Improved retroviral vectors for gene transfer and expression. Biotechniques 7, 980–990.
41. Natorff, R., M. Balinska, and A. Paszewski (1993). At least four regulatory genes control sulphur metabolite repression in *Aspergillus nidulans*. Mol. Gen. Genet. 238, 185–192.
42. Neer, E. J., C. J. Schmidt, R. Nambudripad, and T. F. Smith (1994). The ancient regulatory-protein family of WD-repeat proteins. Nature 371, 297–300.
43. Nellen, D., R. Burke, G. Struhl, and K. Basler (1996). Direct and long range action of a DPP morphogen gradient. Cell 85, 357–368.
44. Robbins, J., B. J. Blondel, D. Gallahan, and R. Callahan (1992). Mouse mammary tumor gene int-3: a member of the Notch gene family transforms mammary epithelial cells. J. Virol. 66, 2594–2599.
45. Rogers, S., R. Wells, and M. Rechsteiner (1986). Amino acid sequences common to rapidly degraded proteins: the PEST hypothesis. Science 234, 364–368.
46. Seydoux, G., and I. Greenwald (1989). Cell autonomy of lin-12 function in a cell fate decision in *C. elegans*. Cell 57, 1237–45.

47. Shen, J., et al. (1997). Skeletel and CNS defects in presenilin-1-deficient mice. Cell 89, 629–639.
48. Sondek, J., A. Bohm, D. G. Lambright, H. E. Hamm, and P. B. Sigler (1996). Crystal structure of a GA protein bg dimer at 2.1 A resolution. Nature 379, 369–374.
49. Struhl, G., K. Fitzgerald, and I. Greenwald (1993). Intrinsic activity of the Lin-12 and Notch intracellular domains in vivo. Cell 74, 331–45.
50. Sundaram, M., and I. Greenwald (1993b). Suppressors of a lin-12 hypomorph define genes that interact with both lin-12 and glp-1 in Caenorhabditis elegans. Genetics 135, 765–783.
51. Thomas, D., L. Kuras, R. Barbey, H. Cherest, P. L. Blaiseau, and Y. Surdin-Kerjan (1995). Met30p, a yeast transcriptional inhibitor that responds to S-adenosylmethionine, is an essential protein with WD40 repeats. Mol. Cell. Biol. 15, 6526–6534.
52. Tuck, S., and I. Greenwald (1995). lin-25, a gene required for vulval induction in Caenorhabditis elegans. Genes Dev. 9, 341–357.
53. Uyttendaele, H., G. Marazzi, G. Wu, Q. Yan, D. Sassoon, and J. Kitajewski (1996). Notch4/int-3, a mammary proto-oncogene, is an endothelial cell-specific mammalian Notch gene. Development 122, 2251–2259.
54. Waterston, R. H., Sulston, J. E., and Coulson, A. R. (1997). The genome. In *C. elegans* II, D. L. Riddle, T. Blumenthal, B. J. Meyer and J. R. Priess, eds. (Cold Spring Harbor Laboratory Press), 23–46.
55. Wilkinson, H. A., K. Fitzgerald, and I. Greenwald (1994). Reciprocal changes in expression of the receptor lin-12 and its ligand lag-2 prior to commitment in a *C. elegans* cell fate decision. Cell 79, 1187–1198.
56. Wilkinson, H. A., and I. Greenwald (1995). Spatial and temporal patterns of lin-12 expression during *C. elegans* hermaphrodite development. Genetics 141, 513–526.
57. Wong, P. C., et al., (1997). Presenilin 1 is required for Notch1 and DII 1 expression in the paraxial mesoderm. Nature 387, 288–291.

What is claimed is:

1. An isolated and purified nucleic acid molecule encoding SEL-10 having an amino acid sequence depicted in SEQ. I.D. No: 2.

2. An isolated and purified nucleic acid molecule encoding SEL-10, said nucleic acid molecule consisting of nucleotides having the sequence depicted in SEQ. I.D. NO: 1.

3. An expression vector comprising the nucleic acid molecule of claim 1.

4. An expression vector comprising the nucleic acid molecule of claim 2.

5. A host cell transformed with the expression vector of claim 3.

6. A host cell transformed with the expression vector of claim 4.

7. The host cell of claim 5 or 6, wherein said host cell is a bacterial cell, insect cell, plant cell, or animal cell.

8. An isolated and purified nucleic acid molecule encoding SEL-10(arl), said nucleic acid molecule consisting of nucleic acids encoding the amino acid residues 1–323 depicted in SEQ. I.D. No. 2.

9. An isolated and purified nucleic acid molecule encoding SEL-10(arl), said nucleic acid molecule consisting of the nucleic acids 1–969 depicted in SEQ. I.D. No. 1.

10. An isolated and purified nucleic acid molecule encoding SEL-10(arl), said nucleic acid molecule consisting of the nucleic acids depicted in SEQ. I.D. No. 1, wherein SEQ. I.D. No. 1 has the mutation G969A.

11. An expression vector comprising the nucleic acid molecule of claim 9.

12. An expression vector comprising the nucleic acid molecule of claim 9.

13. An expression vector comprising the nucleic acid molecule of claim 10.

14. A host cell transformed with the expression vector of claim 11.

15. A host cell transformed with the expression vector of claim 12.

16. A host cell transformed with the expression vector of claim 13.

17. The host cell of claim 14, 15, or 16, wherein said host cell is a bacterial cell, insect cell, plant cell, or animal cell.

18. An isolated and purified nucleic acid molecule encoding SEL-10(ar28), said nucleic acid molecule consisting of nucleic acids encoding the amino acid residues 1–511 depicted in SEQ. I.D. No. 2.

19. An isolated and purified nucleic acid molecule encoding SEL-10(ar28), said nucleic acid molecule consisting of the nucleic acids 1–1533 depicted in SEQ. I.D. No. 1.

20. An isolated and purified nucleic acid molecule encoding SEL-10(ar28), said nucleic acid molecule consisting of the nucleic acids depicted in SEQ. I.D. No. 1, wherein SEQ. I.D. No. 1 has the mutation G1533A.

21. An expression vector comprising the nucleic acid molecule of claim 18.

22. An expression vector comprising the nucleic acid molecule of claim 19.

23. An expression vector comprising the nucleic acid molecule of claim 20.

24. A host cell transformed with the expression vector of claim 21.

25. A host cell transformed with the expression vector of claim 22.

26. A host cell transformed with the expression vector of claim 23.

27. The host cell of claim 24, 25 or 26, wherein said host cell is a bacterial cell, insect cell, plant cell, or animal cell.

28. A vector which comprises an isolated nucleic acid molecule encoding a SEL-10, wherein the vector is the plasmid designated psel-10.8/1A (ATCC Accession No. 209154).

29. A purified and isolated SEL-10 protein, having an amino acid sequence depicted in SEQ ID NO: 2.

30. A purified and isolated SEL-10 (ar1) protein, said protein comprising amino acid residues 1–323 deepicted in SEQ. I.D. No. 2.

31. A purified and isolated SEL-10(ar28) protein, said protein comprising amino acid residues 1–511 depicted in SEQ. I.D. No. 2.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 2481 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 91..1854

(xi) SEQUENCE DESCRIPTION: SEQ ID NO:1:

```
TCATAGTTTT ATCGACTTTC CTTTTGTGTT CAAATTCTTC ATTCCCAGTA GTTTTTGTCC         60

TTTATTCATT TCCAATTCTT TTTCAGCCAT ATG TGG CCA CGA AAT GAT GTA CAC        114
                                 Met Trp Pro Arg Asn Asp Val His
                                   1               5

ATG GAT GAT GGA TCG ATG ACA CCG GAG GAC CAG GAG CCT GTT ACC GAT        162
Met Asp Asp Gly Ser Met Thr Pro Glu Asp Gln Glu Pro Val Thr Asp
     10              15                  20

AAT GAT ATG GAA TAT AAT GAC AAT GGA GAA GAA AGC TCG TAC AGC AAT        210
Asn Asp Met Glu Tyr Asn Asp Asn Gly Glu Glu Ser Ser Tyr Ser Asn
 25              30                  35                  40

GGC TCT TCT TCC AGC TAC AAT GCT GAC AAA TTA TCG TCT TCC AGA CCT        258
Gly Ser Ser Ser Ser Tyr Asn Ala Asp Lys Leu Ser Ser Ser Arg Pro
                 45                  50                  55

TTG CAA CAC AAA CTT GAT TTA TCG GCT TCT CCC TCT CGA AAC AAC GAC        306
Leu Gln His Lys Leu Asp Leu Ser Ala Ser Pro Ser Arg Asn Asn Asp
             60                  65                  70

CTC AAT CCG CGT GTC GAA CAT TTG ATC GCA TTA TTC AAG GAT CTA TCA        354
Leu Asn Pro Arg Val Glu His Leu Ile Ala Leu Phe Lys Asp Leu Ser
         75                  80                  85

AGC GCG GAA CAA ATG GAT GCA TTC ACA CGT CTG CTT CAG GAA TCC AAC        402
Ser Ala Glu Gln Met Asp Ala Phe Thr Arg Leu Leu Gln Glu Ser Asn
     90                  95                 100
```

```
ATG ACA AAT ATT CGA CAG CTG CGT GCC ATT ATT GAA CCC CAT TTC CAG        450
Met Thr Asn Ile Arg Gln Leu Arg Ala Ile Ile Glu Pro His Phe Gln
105             110                 115                 120

CGT GAT TTC CTC TCC TGC CTC CCT GTC GAG CTC GGA ATG AAA ATC CTT        498
Arg Asp Phe Leu Ser Cys Leu Pro Val Glu Leu Gly Met Lys Ile Leu
                125                 130                 135

CAC AAT TTA ACC GGA TAT GAC CTG CTC AAA GTG GCA CAG GTG TCG AAA        546
His Asn Leu Thr Gly Tyr Asp Leu Leu Lys Val Ala Gln Val Ser Lys
            140                 145                 150

AAT TGG AAA TTG ATA TCT GAA ATT GAC AAA ATT TGG AAG AGT CTT GGT        594
Asn Trp Lys Leu Ile Ser Glu Ile Asp Lys Ile Trp Lys Ser Leu Gly
        155                 160                 165

GTC GAA GAG TTT AAA CAT CAT CCA GAT CCC ACA GAC CGA GTT ACT GGT        642
Val Glu Glu Phe Lys His His Pro Asp Pro Thr Asp Arg Val Thr Gly
    170                 175                 180

GCG TGG CAA GGA ACT GCA ATT GCT GCT GGA GTC ACT ATT CCT GAT CAC        690
Ala Trp Gln Gly Thr Ala Ile Ala Ala Gly Val Thr Ile Pro Asp His
185                 190                 195                 200

ATT CAG CCA TGT GAT CTT AAT GTT CAT CGA TTT CTA AAG TTG CAG AAG        738
Ile Gln Pro Cys Asp Leu Asn Val His Arg Phe Leu Lys Leu Gln Lys
                205                 210                 215

TTT GGA GAT ATC TTC GAA CGC GCT GCT GAC AAG TCA CGT TAT CTT CGA        786
Phe Gly Asp Ile Phe Glu Arg Ala Ala Asp Lys Ser Arg Tyr Leu Arg
            220                 225                 230

GCC GAT AAA ATT GAA AAG AAC TGG AAT GCG AAT CCA ATT ATG GGG TCA        834
Ala Asp Lys Ile Glu Lys Asn Trp Asn Ala Asn Pro Ile Met Gly Ser
        235                 240                 245

GCA GTG CTA CGA GGA CAC GAA GAT CAT GTA ATC ACT TGT ATG CAA ATT        882
Ala Val Leu Arg Gly His Glu Asp His Val Ile Thr Cys Met Gln Ile
    250                 255                 260

CAT GAT GAT GTC TTG GTG ACT GGA TCT GAC GAT AAC ACT CTT AAA GTA        930
His Asp Asp Val Leu Val Thr Gly Ser Asp Asp Asn Thr Leu Lys Val
265                 270                 275                 280

TGG TGT ATT GAC AAA GGA GAG GTT ATG TAC ACA CTA GTC GGC CAC ACT        978
Trp Cys Ile Asp Lys Gly Glu Val Met Tyr Thr Leu Val Gly His Thr
                285                 290                 295

GGA GGA GTT TGG ACA TCA CAG ATT TCT CAA TGC GGA AGA TAT ATT GTT       1026
Gly Gly Val Trp Thr Ser Gln Ile Ser Gln Cys Gly Arg Tyr Ile Val
            300                 305                 310

AGC GGG TCC ACT GAT AGA ACT GTA AAA GTT TGG AGT ACT GTA GAT GGT       1074
Ser Gly Ser Thr Asp Arg Thr Val Lys Val Trp Ser Thr Val Asp Gly
        315                 320                 325

TCA CTT CTT CAT ACA CTT CAA GGA CAT ACT TCC ACT GTT CGA TGC ATG       1122
Ser Leu Leu His Thr Leu Gln Gly His Thr Ser Thr Val Arg Cys Met
    330                 335                 340

GCT ATG GCT GGT TCC ATA CTT GTC ACT GGA TCA CGA GAT ACC ACT CTT       1170
Ala Met Ala Gly Ser Ile Leu Val Thr Gly Ser Arg Asp Thr Thr Leu
345                 350                 355                 360

CGT GTA TGG GAC GTA GAA TCC GGA CGT CAC CTG GCA ACT TTA CAT GGC       1218
Arg Val Trp Asp Val Glu Ser Gly Arg His Leu Ala Thr Leu His Gly
                365                 370                 375

CAT CAT GCA GCC GTT CGA TGC GTT CAA TTC GAT GGA ACA ACT GTT GTT       1266
His His Ala Ala Val Arg Cys Val Gln Phe Asp Gly Thr Thr Val Val
            380                 385                 390

TCG GGA GGA TAT GAT TTT ACC GTT AAA ATT TGG AAT GCT CAT ACT GGG       1314
Ser Gly Gly Tyr Asp Phe Thr Val Lys Ile Trp Asn Ala His Thr Gly
        395                 400                 405

AGA TGT ATC CGT ACT CTG ACC GGT CAT AAC AAT AGA GTT TAT TCT CTT       1362
Arg Cys Ile Arg Thr Leu Thr Gly His Asn Asn Arg Val Tyr Ser Leu
    410                 415                 420
```

```
CTC TTT GAA AGC GAG CGA TCG ATC GTG TGC TCT GGC TCT CTG GAC ACT        1410
Leu Phe Glu Ser Glu Arg Ser Ile Val Cys Ser Gly Ser Leu Asp Thr
425                 430                 435                 440

TCA ATT CGC GTG TGG GAT TTT ACA CGA CCG GAA GGC CAA GAA TGT GTG        1458
Ser Ile Arg Val Trp Asp Phe Thr Arg Pro Glu Gly Gln Glu Cys Val
                445                 450                 455

GCT CTT TTG CAA GGA CAC ACC TCA CTT ACA TCC GGA ATG CAA CTT CGA        1506
Ala Leu Leu Gln Gly His Thr Ser Leu Thr Ser Gly Met Gln Leu Arg
            460                 465                 470

GGC AAT ATT CTC GTG TCA TGC AAT GCA GAT AGC CAT GTT AGA GTA TGG        1554
Gly Asn Ile Leu Val Ser Cys Asn Ala Asp Ser His Val Arg Val Trp
        475                 480                 485

GAT ATT CAC GAG GGA ACT TGT GTA CAC ATG CTT TCT GGA CAT CGA TCC        1602
Asp Ile His Glu Gly Thr Cys Val His Met Leu Ser Gly His Arg Ser
    490                 495                 500

GCT ATC ACT TCA CTT CAA TGG TTT GGA CGA AAT ATG GTA GCA ACG AGT        1650
Ala Ile Thr Ser Leu Gln Trp Phe Gly Arg Asn Met Val Ala Thr Ser
505                 510                 515                 520

AGT GAC GAT GGA ACT GTC AAA TTG TGG GAT ATT GAG AGA GGT GCA CTG        1698
Ser Asp Asp Gly Thr Val Lys Leu Trp Asp Ile Glu Arg Gly Ala Leu
                525                 530                 535

ATT CGA GAT CTA GTA ACT TTG GAT TCT GGA GGC AAT GGT GGC TGT ATT        1746
Ile Arg Asp Leu Val Thr Leu Asp Ser Gly Gly Asn Gly Gly Cys Ile
            540                 545                 550

TGG AGA CTT TGT TCT ACT TCT ACG ATG CTA GCG TGT GCA GTC GGA TCT        1794
Trp Arg Leu Cys Ser Thr Ser Thr Met Leu Ala Cys Ala Val Gly Ser
        555                 560                 565

CGT AAC AAC ACC GAG GAG ACC AAA GTT ATC CTT CTC GAC TTT GAT GCT        1842
Arg Asn Asn Thr Glu Glu Thr Lys Val Ile Leu Leu Asp Phe Asp Ala
    570                 575                 580

GTA TAC CCT TAA CGAATTCTCG AATCTCTGCC CCTGTACATA GAATGTTCTT           1894
Val Tyr Pro *
585

GCTTAGGAAC TAATATTGTA CACGATGCCC TCATTTTTAA ATCAACAATG CTATCATATC     1954

ATGGAATATA GTCAAAAGCC AACAGTATTG AAACGTCAAA TTTGAGGAAA AACGAATTTA     2014

TGTGTCTATT CAACTCGTTA TATCCCGGCC CGCCACTATA ATTTTTCTTT TTTTTACTAT     2074

TTTTTGTCAG ATTCTGTCTC ACACTCTTCT CTTTCTCTTT TCGATTGTTT CCCATTAAGT     2134

TATCGGGTTT GATTGATTTT ATATTTTTAT TCAAATGATG GGCTCACTAC TCCCAGATTT     2194

TGATTTCCTT TATACAATAG TTCAGTCAGT ATGTTAGTCC TTATGTGACT TCTTTTTGAT     2254

CTAATGAGCT TTTTAGTCCC TGTCGGTTCC CTCTTTTTTC GCTTTCATTT TTCGTAAAAA     2314

CTACTTGTCA AAATTCAAAG TTCTACCCTC GACATTGCCT TTTTTAAAAT TTTTGTCTTC     2374

GTTTTATCGA CTTATGCCAG ACGTCATTCG ATTAAGTAGG TTAATAACAA TTATTTCATA     2434

ATAATAAATA TCGATTCGTG TCATCCGTCT ATATGTGATT TTCTTTT                   2481

(2) INFORMATION FOR SEQ ID NO:2:

(i) SEQUENCE CHARACTERISTICS:
        (A) LENGTH: 587 amino acids
        (B) TYPE: amino acid
        (D) TOPOLOGY: linear (ii) MOLECULE TYPE: protein (xi) SEQUENCE DESCRIPTION: SEQ ID NO:2:

Met Trp Pro Arg Asn Asp Val His Met Asp Asp Gly Ser Met Thr Pro
1               5                   10                  15
```

```
Glu Asp Gln Glu Pro Val Thr Asp Asn Asp Met Glu Tyr Asn Asp Asn
             20                  25                  30

Gly Glu Glu Ser Ser Tyr Ser Asn Gly Ser Ser Ser Tyr Asn Ala
         35                  40                  45

Asp Lys Leu Ser Ser Ser Arg Pro Leu Gln His Lys Leu Asp Leu Ser
     50                  55                  60

Ala Ser Pro Ser Arg Asn Asn Asp Leu Asn Pro Arg Val Glu His Leu
 65                  70                  75                  80

Ile Ala Leu Phe Lys Asp Leu Ser Ser Ala Glu Gln Met Asp Ala Phe
                 85                  90                  95

Thr Arg Leu Leu Gln Glu Ser Asn Met Thr Asn Ile Arg Gln Leu Arg
             100                 105                 110

Ala Ile Ile Glu Pro His Phe Gln Arg Asp Phe Leu Ser Cys Leu Pro
         115                 120                 125

Val Glu Leu Gly Met Lys Ile Leu His Asn Leu Thr Gly Tyr Asp Leu
     130                 135                 140

Leu Lys Val Ala Gln Val Ser Lys Asn Trp Lys Leu Ile Ser Glu Ile
145                 150                 155                 160

Asp Lys Ile Trp Lys Ser Leu Gly Val Glu Glu Phe Lys His His Pro
                165                 170                 175

Asp Pro Thr Asp Arg Val Thr Gly Ala Trp Gln Gly Thr Ala Ile Ala
            180                 185                 190

Ala Gly Val Thr Ile Pro Asp His Ile Gln Pro Cys Asp Leu Asn Val
        195                 200                 205

His Arg Phe Leu Lys Leu Gln Lys Phe Gly Asp Ile Phe Glu Arg Ala
    210                 215                 220

Ala Asp Lys Ser Arg Tyr Leu Arg Ala Asp Lys Ile Glu Lys Asn Trp
225                 230                 235                 240

Asn Ala Asn Pro Ile Met Gly Ser Ala Val Leu Arg Gly His Glu Asp
                245                 250                 255

His Val Ile Thr Cys Met Gln Ile His Asp Asp Val Leu Val Thr Gly
            260                 265                 270

Ser Asp Asp Asn Thr Leu Lys Val Trp Cys Ile Asp Lys Gly Glu Val
        275                 280                 285

Met Tyr Thr Leu Val Gly His Thr Gly Gly Val Trp Thr Ser Gln Ile
    290                 295                 300

Ser Gln Cys Gly Arg Tyr Ile Val Ser Gly Ser Thr Asp Arg Thr Val
305                 310                 315                 320

Lys Val Trp Ser Thr Val Asp Gly Ser Leu Leu His Thr Leu Gln Gly
                325                 330                 335

His Thr Ser Thr Val Arg Cys Met Ala Met Ala Gly Ser Ile Leu Val
            340                 345                 350

Thr Gly Ser Arg Asp Thr Thr Leu Arg Val Trp Asp Val Glu Ser Gly
        355                 360                 365

Arg His Leu Ala Thr Leu His Gly His Ala Ala Val Arg Cys Val
    370                 375                 380

Gln Phe Asp Gly Thr Thr Val Val Ser Gly Gly Tyr Asp Phe Thr Val
385                 390                 395                 400

Lys Ile Trp Asn Ala His Thr Gly Arg Cys Ile Arg Thr Leu Thr Gly
                405                 410                 415

His Asn Asn Arg Val Tyr Ser Leu Leu Phe Glu Ser Glu Arg Ser Ile
            420                 425                 430
```

```
Val Cys Ser Gly Ser Leu Asp Thr Ser Ile Arg Val Trp Asp Phe Thr
            435                 440                 445

Arg Pro Glu Gly Gln Glu Cys Val Ala Leu Leu Gln Gly His Thr Ser
        450                 455                 460

Leu Thr Ser Gly Met Gln Leu Arg Gly Asn Ile Leu Val Ser Cys Asn
465                 470                 475                 480

Ala Asp Ser His Val Arg Val Trp Asp Ile His Glu Gly Thr Cys Val
                485                 490                 495

His Met Leu Ser Gly His Arg Ser Ala Ile Thr Ser Leu Gln Trp Phe
                500                 505                 510

Gly Arg Asn Met Val Ala Thr Ser Ser Asp Asp Gly Thr Val Lys Leu
            515                 520                 525

Trp Asp Ile Glu Arg Gly Ala Leu Ile Arg Asp Leu Val Thr Leu Asp
        530                 535                 540

Ser Gly Gly Asn Gly Gly Cys Ile Trp Arg Leu Cys Ser Thr Ser Thr
545                 550                 555                 560

Met Leu Ala Cys Ala Val Gly Ser Arg Asn Asn Thr Glu Glu Thr Lys
                565                 570                 575

Val Ile Leu Leu Asp Phe Asp Ala Val Tyr Pro
            580                 585

(2) INFORMATION FOR SEQ ID NO:3:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Leu Pro Val Glu Leu Gly Met Lys Ile Leu His Asn Leu Thr Gly Tyr
1               5                   10                  15

Asp Leu Leu Lys Val Ala Gln Val Ser Lys Asn Trp Lys Leu Ile Ser
            20                  25                  30

Glu Ile Asp Lys Ile Trp Lys Ser Leu Gly
        35                  40

(2) INFORMATION FOR SEQ ID NO:4:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Leu Pro Phe Glu Ile Ser Leu Lys Ile Phe Asn Tyr Leu Gln Phe Glu
1               5                   10                  15

Asp Ile Ile Asn Ser Leu Gly Val Ser Gln Asn Trp Asn Lys Ile Ile
            20                  25                  30

Arg Lys Ser Thr Ser Leu Trp Lys Lys Leu Leu
        35                  40
```

(2) INFORMATION FOR SEQ ID NO:5:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Leu Pro Leu Glu Leu Ser Phe Tyr Leu Leu Lys Trp Leu Asp Pro Gln
 1               5                  10                  15

Thr Leu Leu Thr Cys Cys Leu Val Ser Lys Gln Arg Asn Lys Val Ile
            20                  25                  30

Ser Ala Cys Thr Glu Val Trp Gln Thr Ala Cys
        35                  40
```

(2) INFORMATION FOR SEQ ID NO:6:

(i) SEQUENCE CHARACTERISTICS:
        (A) LENGTH: 209 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Gly His Glu Asp His Val Ile Thr Cys Met Gln Ile His Asp Asp Val
 1               5                  10                  15

Leu Val Thr Gly Ser Asp Asp Asn Thr Leu Lys Val Trp Cys Gly His
            20                  25                  30

Thr Gly Gly Val Trp Thr Ser Gln Ile Ser Gln Cys Gly Arg Tyr Ile
        35                  40                  45

Val Ser Gly Ser Thr Asp Arg Thr Val Lys Val Trp Ser Gly His Thr
50                  55                  60

Ser Thr Val Arg Cys Met Ala Met Ala Gly Ser Ile Leu Val Thr Gly
65                  70                  75                  80

Ser Arg Asp Thr Thr Leu Arg Val Trp Asp Gly His His Ala Ala Val
                85                  90                  95

Arg Cys Val Gln Phe Asp Gly Thr Thr Val Val Ser Gly Gly Tyr Asp
            100                 105                 110

Phe Thr Val Lys Ile Trp Asn Gly His Asn Asn Arg Val Tyr Ser Leu
        115                 120                 125

Leu Phe Glu Ser Glu Arg Ser Ile Val Cys Ser Gly Ser Leu Asp Thr
130                 135                 140

Ser Ile Arg Val Trp Asp Gly His Thr Ser Leu Thr Ser Gly Met Gln
145                 150                 155                 160

Leu Arg Gly Asn Ile Leu Val Ser Cys Asn Ala Asp Ser His Val Arg
                165                 170                 175

Val Trp Asp Gly His Arg Ser Ala Ile Thr Ser Leu Gln Trp Phe Gly
            180                 185                 190

Arg Asn Met Val Ala Thr Ser Ser Asp Asp Gly Thr Val Lys Leu Trp
        195                 200                 205

Asp
```

-continued (2) INFORMATION FOR SEQ ID NO:7:

(i) SEQUENCE CHARACTERISTICS:
        (A) LENGTH: 212 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Gly His Met Thr Ser Val Ile Thr Cys Leu Gln Phe Glu Asp Asn Tyr
1               5                   10                  15

Val Ile Thr Gly Ala Asp Asp Lys Met Ile Arg Val Tyr Asp Gly His
            20                  25                  30

Asp Gly Gly Val Trp Ala Leu Lys Tyr Ala His Gly Gly Ile Leu Val
        35                  40                  45

Ser Gly Ser Thr Asp Arg Thr Val Arg Val Trp Asp Gly His Asn Ser
    50                  55                  60

Thr Val Arg Cys Leu Asp Ile Val Glu Tyr Lys Asn Ile Lys Tyr Ile
65                  70                  75                  80

Val Thr Ser Gly Arg Asp Asn Thr Leu His Val Trp Lys Gly His Met
                85                  90                  95

Ala Ser Val Arg Thr Val Ser Gly His Gly Asn Ile Val Val Ser Gly
            100                 105                 110

Ser Tyr Asp Asn Thr Leu Ile Val Trp Asp Gly His Thr Asp Arg Ile
        115                 120                 125

Tyr Ser Thr Ile Tyr Asp His Glu Arg Lys Arg Cys Ile Ser Ala Ser
    130                 135                 140

Met Asp Thr Thr Ile Arg Ile Trp Asp Gly His Thr Ala Leu Val Gly
145                 150                 155                 160

Leu Leu Arg Leu Ser Asp Lys Phe Leu Val Ser Ala Ala Asp Gly
                165                 170                 175

Ser Ile Arg Gly Trp Asp His His Thr Asn Leu Ser Ala Ile Thr Thr
            180                 185                 190

Phe Tyr Val Ser Asp Asn Ile Leu Val Ser Gly Ser Glu Asn Gln Phe
        195                 200                 205

Asn Ile Tyr Asn
        210
```